(12) United States Patent
Amberg et al.

(10) Patent No.: US 6,448,248 B1
(45) Date of Patent: Sep. 10, 2002

(54) HETEROCYCLIC CARBOXYLIC ACID DERIVATIVES, THE PRODUCTION AND USE THEREOF AS ENDOTHELIN RECEPTOR ANTAGONISTS

(75) Inventors: Wilhelm Amberg, Schwetzingen; Rolf Jansen; Andreas Kling, both of Mannheim; Dagmar Klinge, Heidelberg; Hartmut Riechers, Neustadt; Stefan Hergenröder, Mainz; Manfred Raschack, Weisenheim; Liliane Unger, Ludwigshafen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/319,876
(22) PCT Filed: Dec. 4, 1997
(86) PCT No.: PCT/EP97/06778
§ 371 (c)(1), (2), (4) Date: Jun. 14, 1999
(87) PCT Pub. No.: WO98/27070
PCT Pub. Date: Jun. 25, 1998

(30) Foreign Application Priority Data

Dec. 18, 1996 (DE) .......................... 196 52 763
Jan. 13, 1997 (DE) .......................... 197 00 884

(51) Int. Cl.[7] ............... C07D 253/065; A61K 31/53
(52) U.S. Cl. ............... 514/242; 514/243; 544/182; 544/183; 544/184
(58) Field of Search ............... 544/182, 183, 544/184; 548/250; 514/242, 243

(56) References Cited

U.S. PATENT DOCUMENTS 5,254,548 A  * 10/1993 Wermuth et al. ............ 514/242

FOREIGN PATENT DOCUMENTS

| DE | 19533023 | * | 7/1995 |
| DE | 195 33023 | | 4/1996 |
| DE | 196 14533 | | 10/1997 |
| DE | 19614534 | | 10/1997 |
| DE | 196 14542 | | 10/1997 |
| HU | 172769 | | 5/1975 |
| WO | 96/11914 | | 4/1996 |
| WO | 97/38980 | | 10/1997 |
| WO | 97/38981 | | 10/1997 |
| WO | 97/38982 | | 10/1997 |

OTHER PUBLICATIONS

J. Med. Chem. 1996, 39 2123–2128, Riechers.

* cited by examiner

*Primary Examiner*—Deepak R. Rao
(74) *Attorney, Agent, or Firm*—Keil & Weinkauf

(57) ABSTRACT

The present invention relates to carboxylic acid derivatives of the formula I

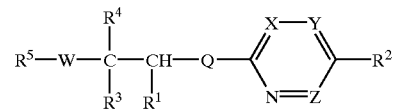

where the substituents have the meanings explained in the description, and to preparation and use as endothelin receptor antagonists.

6 Claims, No Drawings

HETEROCYCLIC CARBOXYLIC ACID DERIVATIVES, THE PRODUCTION AND USE THEREOF AS ENDOTHELIN RECEPTOR ANTAGONISTS

This application is a 371 of PCT/EP 97/06778 filed Dec. 4, 1997.

The present invention relates to novel carboxylic acid derivatives, their preparation and use.

Endothelin is a peptide made up of 21 amino acids, which is synthesized and released by vascular endothelin. Endothelin exists in three isoforms, ET-1, ET-2 and ET-3. In the following, endothelin or ET designates one or all isoforms of endothelin. Endothelin is a potent vasoconstrictor and has a strong effect on the vascular tone. It is known that this vasoconstriction is caused by the binding of endothelin to its receptor (Nature, 332 (1988), 411–415; FEBS Letters, 231 (1988), 440–444, and Biochem. Biophys. Res. Commun., 154 (1988), 868–875).

Increased or abnormal release of endothelin causes a lasting vascular contraction in peripheral, renal and cerebral blood vessels which can lead to illnesses. As reported in the literature, endothelin is involved in a number of illnesses. These include: hypertension, acute myocardial infarct, pulmonary hypertension, Raynaud's Syndrome, cerebral vasospasms, stroke, benign prostate hypertrophy, atherosclerosis and asthma (J. Vascular Med. Biology 2 (1990), 207, J. Am. Med. Association 264 (1990), 2868, Nature 344 (1990), 114, N. Engl. J. Med. 322 (1989), 205, N. Engl. J. Med. 328 (1993), 1732, Nephron 66 (1994), 373, Stroke 25 (1994), 904, Nature 365 (1993), 759, J. Mol. Cell. Cardiol. 27 (1995), A234; Cancer Research 56 (1996), 663).

At least two endothelin receptor subtypes, $ET_A$ and $ET_B$ receptors, are at present described in the literature (Nature 348 (1990), 730, Nature 348 (1990), 732). Accordingly, substances which inhibit the binding of endothelin to one or to both receptors should antagonize physiological effects of endothelin and therefore be useful pharmaceuticals.

It is an object of the present invention to make available endothelin receptor antagonists which bind to the $ET_A$ and/or the $ET_B$ receptors.

The invention relates to carboxylic acid derivatives of the formula I

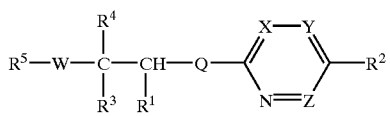

[lacuna] $R^1$ is tetrazole or a group

where R has the following meanings:
a) a radical $OR^6$, where $R^6$ is:
  hydrogen, the cation of an alkali metal, the cation of an alkaline earth metal, a physiologically tolerable organic ammonium ion such as tertiary $C_1$–$C_4$-alkylammonium or the ammonium ion;
  $C_3$–$C_8$-cycloalkyl, $C_1$–$C_8$-alkyl, $CH_2$-phenyl which can be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)_2$;
  a $C_3$–$C_8$-alkenyl or a $C_3$–$C_8$-alkynyl group, it being possible for these groups in turn to carry one to five halogen atoms;
  $R^6$ can furthermore be a phenyl radical which can carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $NH(C_1$–$C_4$-alkyl), $N(C_1$–$C_4$-alkyl)_2$;
b) a 5-membered heteroaromatic linked via a nitrogen atom, such as pyrrolyl, pyrazolyl, imidazolyl or triazolyl, which can carry one to two halogen atoms, or one to two $C_1$–$C_4$-alkyl or one to two $C_1$–$C_4$-alkoxy groups;
c) a group

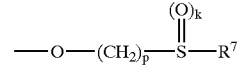

where k [lacuna] assume the values 0, 1 and 2, p can assume the values 1, 2, 3 and 4 and $R^7$ is
  $C_1$–$C_4$-alkyl, $C_3$–$C_8$-cycloalkyl, $C_3$–$C_8$-alkenyl, $C_3$–$C_8$-alkynyl or phenyl, which can be substituted by one or more, eg. one to three, of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, $NH(C_1$–$C_4$-alkyl), $N(C_1$–$C_4$-alkyl)_2$;
d) a radical

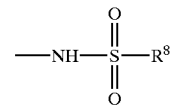

where $R^8$ is:
  $C_1$–$C_4$-alkyl, $C_3$–$C_8$-alkenyl, $C_3$–$C_8$-alkynyl, $C_3$–$C_8$-cycloalkyl, it being possible for these radicals to carry a $C_1$–$C_4$-alkoxy, $C_1$–$C_4$-alkylthio and/or a phenyl radical as mentioned under c);
  $C_1$–$C_4$-haloalkyl or unsubstituted or substituted phenyl, in particular as mentioned under c).

The other substituents have the following meanings:
X is nitrogen or methine; with the proviso that if X=nitrogen then Z=nitrogen and if X=methine then at least one of the ring members Y or Z is nitrogen;
Y is nitrogen or $CR^9$;
Z is nitrogen or $CR^{10}$;
$R^2$ is $C_1$–$C_4$-alkyl, $C_2$–$C_4$-alkenyl, $C_2$–$C_4$-alkynyl, it being possible for these radicals each to be mono- or polysubstituted by: halogen, hydroxyl, mercapto, carboxyl, cyano, amino, $C_1$–$C_4$-alkoxy;
  hydrogen, halogen, $C_1$–$C_4$-alkoxy, $C_1$–$C_4$-haloalkoxy, $C_3$–$C_6$-alkenyloxy, $C_3$–$C_6$-alkynyloxy, $C_1$–$C_4$-alkylthio, $C_1$–$C_4$-alkylcarbonyl, $C_1$–$C_4$-alkoxycarbonyl, $NH(C_1$–$C_4$-alkyl), $N(C_1$–$C_4$-alkyl)_2$, hydroxyl, carboxyl, cyano, amino, mercapto;
  or $CR^2$ together with $CR^9$ or $CR^{10}$ forms a 5- or 6-membered alkylene or alkenylene ring which can be substituted by one or two $C_1$–$C_4$-alkyl groups, and where in each case one or more methylene groups can be replaced by oxygen, sulfur, —NH or —$N(C_1$–$C_4$-alkyl);
$R^3$ and $R^4$ (which can be identical or different) are:
phenyl or naphthyl, which can be substituted by one or more of the following radicals: halogen, nitro, cyano, hydroxyl, mercapto, $C_1$–$C_4$-alkyl, $C_2$–$C_4$-alkenyl, $C_2$–$C_4$-alkynyl, $C_1$–$C_4$-haloalkyl, $C_1$–$C_4$-alkoxy, phenoxy, $C_1$–$C_4$-haloalkoxy, $C_1$–$C_4$-alkylthio, amino, NH($C_1$–$C_4$-alkyl), N($C_1$–$C_4$-alkyl)$_2$ or phenyl, which can be mono- or polysubstituted, eg. mono- to trisubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or phenyl or naphthyl, which are connected to one another in the ortho position via a direct bond, a methylene, ethylene or ethenylene group, an oxygen or sulfur atom or an SO$_2$—, NH— or N-alkyl group;

$C_3$–$C_8$-cycloalkyl, it being possible for these radicals in each case to be mono- or polysubstituted by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy;

$R^5$ is hydrogen, $C_1$–$C_8$-alkyl, $C_3$–$C_8$-alkenyl or $C_3$–$C_8$-alkynyl, it being possible for these radicals in each case to be mono- or polysubstituted by: halogen, hydroxyl, mercapto, carboxyl, nitro, amino, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_3$–$C_8$-alkylcarbonylalkyl, NH($C_1$–$C_4$-alkyl), N($C_1$–$C_4$-alkyl)$_2$, $C_3$–$C_8$-cycloalkyl, heteroaryloxy or heteroaryl, which is five-or six-membered, comprising one to three nitrogen atoms and/or a sulfur or oxygen atom, phenoxy or phenyl, it being possible for the aryl radicals mentioned in turn to be mono- or polysubstituted, eg. mono- to trisubstituted by halogen, hydroxyl, mercapto, carboxyl, nitro, cyano, $C_1$–$C_4$-alkyl, $C_1$–$C_4$-haloalkyl, $C_1$–$C_4$-alkoxy, $C_1$–$C_4$-haloalkoxy, amino, NH($C_1$–$C_4$-alkyl), N($C_1$–$C_4$-alkyl)$_2$ or $C_1$–$C_4$-alkylthio;

phenyl or naphthyl, which in each case can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino, $C_1$–$C_4$-dialkylamino, dioxomethylene or dioxoethylene;

a five- or six-membered heteroaromatic, comprising one to three nitrogen atoms and/or a sulfur or oxygen atom, which can carry one to four halogen atoms and/or one to two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_3$–$C_8$-cycloalkyl, it being possible for these radicals in each case to be mono- or polysubstituted by: halogen, hydroxyl, mercapto, carboxyl, nitro, cyano, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy;

$R^9$ and $R^{10}$ (which can be identical or different) are:

hydrogen, halogen, $C_1$–$C_4$-alkoxy, $C_1$–$C_4$-haloalkoxy, $C_3$–$C_6$-alkenyloxy, $C_3$–$C_6$-alkynyloxy, $C_1$–$C_4$-alkylthio, $C_1$–$C_4$-alkylcarbonyl, $C_1$–$C_4$-alkoxycarbonyl, NH$_2$, NH($C_1$–$C_4$-alkyl), N($C_1$–$C_4$-alkyl)$_2$;

$C_1$–$C_4$-alkyl, $C_2$–$C_4$-alkenyl, $C_2$–$C_4$-alkynyl, it being possible for these radicals to be substituted by halogen, hydroxyl, mercapto, carboxyl, cyano;

or CR$^9$ or CR$^{10}$ is linked with CR$^2$ as indicated under R$^2$ to give a 5- or 6-membered ring;

W is sulfur, oxygen or a single bond;

Q is oxygen or nitrogen; with the proviso that if Q=nitrogen then W is a single bond.

In this context and subsequently the following definitions apply:

an alkali metal is, for example, lithium, sodium, potassium;

an alkaline earth metal is, for example, calcium, magnesium, barium;

organic ammonium ions are protonated amines such as, for example, ethanolamine, diethanolamine, ethylendiamine diethylamine or piperazine;

$C_3$–$C_8$-cycloalkyl is, for example, cyclopropyl, cyclobutyl, cyclopentyl, cyclohexyl, cycloheptyl or cyclooctyl;

$C_1$–$C_4$-haloalkyl can be linear or branched such as, for example, fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

$C_1$–$C_4$-haloalkoxy can be linear or branched such as, for example, difluoromethoxy, trifluoromethoxy, chlorodifluoromethoxy, 1-fluoroethoxy, 2,2-difluoroethoxy, 1,1,2,2-tetrafluoroethoxy, 2,2,2-trifluoroethoxy, 2-chloro-1,1,2-trifluoroethoxy, 2-fluoroethoxy or pentafluoroethoxy;

$C_1$–$C_4$-alkyl can be linear or branched such as, for example, ethyl, ethyl, 1-propyl, 2-propyl, 2-methyl-2-propyl, 2-methyl-1-propyl, 1-butyl or 2-butyl;

$C_2$–$C_4$-alkenyl can be linear or branched such as, for example, ethenyl, 1-propen-3-yl, 1-propen-2-yl, 1-propen-1-yl, 2-methyl-1-propenyl, 1-butenyl or 2-butenyl;

$C_2$–$C_4$-alkynyl can be linear or branched such as, for example, ethynyl, 1-propyn-1-yl, 1-propyn-3-yl, 1-butyn-4-yl or 2-butyn-4-yl;

$C_1$–$C_4$-alkoxy can be linear or branched such as, for example, methoxy, ethoxy, propoxy, 1-methylethoxy, butoxy, 1-methylpropoxy, 2-methylpropoxy or 1,1-dimethylethoxy;

$C_3$–$C_6$-alkenyloxy can be linear or branched such as, for example, allyloxy, 2-buten-1-yloxy or 3-buten-2-yloxy;

$C_3$–$C_6$-alkynyloxy can be linear or branched such as, for example, 2-propyn-1-yloxy, 2-butyn-1-yloxy or 3-butyn-2-yloxy;

$C_1$–$C_4$-alkylthio can be linear or branched such as, for example, methylthio, ethylthio, propylthio, 1-methylethylthio, butylthio, 1-methylpropylthio, 2-methylpropylthio or 1,1-dimethylethylthio;

$C_1$–$C_4$-alkylcarbonyl can be linear or branched such as, for example, acetyl, ethylcarbonyl or 2-propylcarbonyl;

$C_1$–$C_4$-alkoxycarbonyl can be linear or branched such as, for example, methoxycarbonyl, ethoxycarbonyl, n-propoxycarbonyl, i-propoxycarbonyl or n-butoxycarbonyl;

$C_3$–$C_8$-alkylcarbonylalkyl can be linear or branched, for example 2-oxoprop-1-yl, 3-oxobut-1-yl or 3-oxobut-2-yl;

$C_1$–$C_8$-alkyl can be linear or branched such as, for example, $C_1$–$C_4$-alkyl, pentyl, hexyl, heptyl or octyl;

$C_3$–$C_8$-alkenyl can be linear or branched such as, for example, 1-propen-3-yl, 1-propen-2-yl, 1-propen-1-yl, 2-methyl-1-propenyl, 1-buten-4-yl, 2-buten-3-yl, 1-penten-5-yl, 1-hexen-6-yl, 3-hexen-6-yl, 2-hepten-7-yl or 1-octen-8-yl;

$C_3$–$C_8$-alkynyl can be linear or branched such as, for example, 1-propyn-1-yl, 1-propyn-3-yl, 1-butyn-4-yl, 2-butyn-4-yl, 2-pentyn-5-yl, 3-hexyn-6-yl, 3-heptyn-7-yl, 2-octyn-8-yl;

halogen is, for example, fluorine, chlorine, bromine, iodine.

The invention further relates to those compounds from which the compounds of the formula I can be released (prodrugs).

Those prodrugs are preferred in which the release proceeds under conditions of the type which prevail in certain body compartments, eg. in the stomach, intestine, blood circulation, liver.

The compounds I and also the intermediates for their preparation, such as, for example, II, III, IV and V, can have one or more asymmetrically substituted carbon atoms. Compounds of this type can be present as pure enantiomers or pure diastereomers or as a mixture thereof. The use of an enantiomeric pure compound as the active compound is preferred.

The invention further relates to the use of the abovementioned carboxylic acid derivatives for the production of drugs, in particular for the production of inhibitors for $ET_A$ and/or $ET_B$ receptors. The compounds according to the invention are suitable as antagonists, as were defined at the outset.

The preparation of the compounds of the general formula IV, where W is sulfur or oxygen and Q is oxygen (IVa) can be carried out, also in enantiomerically pure form, as described in WO 96/11914.

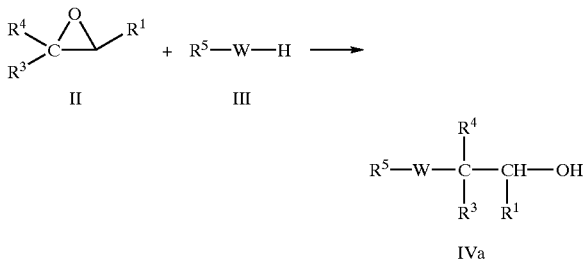

Compounds of the general formula III are either known or can be synthesized, for example, by reduction of the corresponding carboxylic acids or their esters, or by other generally known methods.

The compounds of the general formula IV, where W is a single bond and Q is oxygen (VIb), can be prepared both in racemic and in enantiomerically pure form as described in DE 19614533.3.

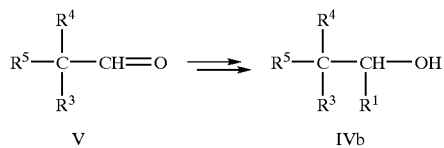

On the other hand, the compounds of the general formula IV, where W is a single bond and Q is nitrogen (IVc) can be prepared both in racemic form and in enantiomerically pure form as described in DE 19536891.6.

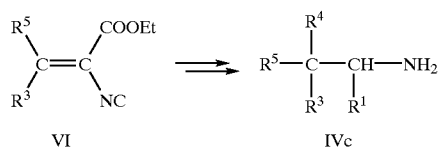

The compounds according to the invention, where the substituents have the meanings indicated under the general formula I, can be prepared, for example, by reacting the carboxylic acid derivatives of the general formula IV, in which the substituents have the meanings indicated, with compounds of the general formula VII.

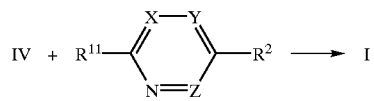

In formula VII, $R^{11}$ is halogen or $R^{12}$—$SO_2$—, it being possible for $R^{12}$ to be $C_1$–$C_4$-alkyl, $C_1$–$C_4$-haloalkyl or phenyl, and for X, Y and Z the conditions mentioned at the outset apply. The reaction preferably takes place in an inert solvent or diluent with addition of a suitable base, ie. of a base which brings about deprotonation of the intermediate IV, in a temperature range from room temperature up to the boiling point of the solvent.

Compounds of the type I where $R^1$=COOH can furthermore be obtained directly if the intermediate IV, where $R^1$ is COOH, is deprotonated using two equivalents of a suitable base and reacted with compounds of the general formula V. Here also, the reaction takes place in an inert solvent and in a temperature range from room temperature up to the boiling point of the solvent.

Examples of solvents or diluents of this type are aliphatic, alicyclic and aromatic hydrocarbons, which in each case can be free or chlorinated, such as, for example, hexane, cyclohexane, petroleum ether, naphtha, benzene, toluene, xylene, methylene chloride, chloroform, carbon tetrachloride, ethyl chloride and trichloroethylene, ethers, such as, for example, diisopropyl ether, dibutyl ether, methyl tert-butyl ether, propylene oxide, dioxane and tetrahydrofuran, nitrites, such as, for example, acetonitrile and propionitrile, acid amides, such as, for example, dimethylformamide, dimethylacetamide and N-methylpyrrolidone, sulfoxides and sulfones, such as, for example, dimethyl sulfoxide and sulfolane.

Compounds of the formula VII are known, in some cases commercially available or can be prepared in a generally known manner (eg. in a similar manner to J. Org. Chem. 52 (1987), 4280).

The base used can be an alkali metal or alkaline earth metal hydride, such as sodium hydride, potassium hydride or calcium hydride, a carbonate such as an alkali metal carbonate, eg. sodium or potassium carbonate, an alkali metal or alkaline earth metal hydroxide such as sodium or potassium hydroxide, an organometallic compound such as butyllithium or an alkali metal amide such as lithium diisopropylamide or lithium amide.

Compounds of the formula I can also be prepared by starting from the corresponding carboxylic acids, ie. compounds of the formula I where $R^1$ is COOH, and first converting these in a customary manner into an activated form such as an acid halide, an anhydride or imidazolide and then reacting this with an appropriate hydroxyl compound $HOR^7$. This reaction can be carried out in the customary solvents and often requires the addition of a base, those mentioned above being suitable. These two steps can also be simplified, for example, by allowing the carboxylic acid to act on the hydroxyl compound in the presence of a dehydrating agent such as a carbodiimide.

Moreover, compounds of the formula I can also be prepared by starting from the salts of the corresponding carboxylic acids, ie. from compounds of the formula I where $R^1$ is COR and R is OM, it being possible for M to be an alkali metal cation or the equivalent of an alkaline earth metal cation. These salts can be reacted with many compounds of the formula R-A, A being a customary nucleofugic leaving group, for example halogen such as chlorine, bromine, iodine or, if desired, aryl- or alkylsulfonyl substituted by halogen, alkyl or haloalkyl, such as, for example, toluenesulfonyl and methylsulfonyl or another equivalent leaving group. Compounds of the formula R-A having a reactive substituent A are known or easy to obtain using the general expert knowledge. This reaction can be carried out in the customary solvents and is advantageously performed with addition of a base, those mentioned above being suitable.

Compounds of the formula I where $R^1$ is tetrazole can be prepared as described in WO 96/11914.

With respect to the biological action, carboxylic acid derivatives of the general formula I, both as pure enantiomers and pure diastereomers or as a mixture thereof, are preferred where the substituents have the following meanings:

X is nitrogen or methine; with the proviso that if X=nitrogen then Z=nitrogen and if X=methine then at least one of the ring members Y or Z=nitrogen;

Y is nitrogen or $CR^9$;

Z is nitrogen or $CR^{10}$;

$R^2$ is $C_1$–$C_4$-alkyl, $C_2$–$C_4$-alkenyl, it being possible for these radicals each to be mono- to trisubstituted by: halogen, hydroxyl, mercapto;

hydrogen, halogen, $C_1$–$C_4$-alkoxy, $C_1$–$C_4$-haloalkoxy, $C_1$–$C_4$-alkylthio, $C_1$–$C_4$-alkoxycarbonyl, NH($C_1$–$C_4$-alkyl), N($C_1$–$C_4$-alkyl)$_2$, hydroxyl;

or $CR^2$, together with $CR^9$ or $CR^{10}$, forms a 5- or 6-membered alkylene or alkenylene ring which can be substituted by one or two $C_1$–$C_4$-alkyl groups, and where in each case one or more methylene groups can be replaced by oxygen, sulfur, —NH or —N($C_1$–$C_4$-alkyl);

$R^3$ and $R^4$ (which can be identical or different) are:

phenyl or naphthyl, it being possible for these radicals to be mono- to trisubstituted by: halogen, cyano, hydroxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, amino, NH($C_1$–$C_4$-alkyl), N($C_1$–$C_4$-alkyl)$_2$ or phenyl, which can be mono- to trisubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio; or phenyl or naphthyl, which are bonded to one another in the ortho position via a direct bond, a methylene, ethylene or ethenylene group, an oxygen or sulfur atom or an $SO_2$—, NH— or N-alkyl group;

$C_3$–$C_8$-cycloalkyl, it being possible for these radicals in each case to be mono- to trisubstituted by: halogen, hydroxyl, mercapto, cyano, $C_1$–$C_4$-alkyl, $C_1$–$C_4$-alkoxy, $C_1$–$C_4$-alkylthio, $C_1$–$C_4$-haloalkoxy;

$R^5$ is hydrogen, $C_1$–$C_8$-alkyl, $C_3$–$C_8$-alkenyl or $C_3$–$C_8$-alkynyl, it being possible for these radicals in each case to be mono- to trisubstituted by: halogen, hydroxyl, mercapto, carboxyl, amino, cyano, $C_1$–$C_4$-alkoxy, $C_1$–$C_4$-alkylthio, $C_1$–$C_4$-haloalkoxy, $C_1$–$C_4$-alkylcarbonyl, $C_1$–$C_4$-alkoxycarbonyl, NH($C_1$–$C_4$-alkyl), N($C_1$–$C_4$-alkyl)$_2$, $C_3$–$C_8$-cycloalkyl, heteroaryloxy or heteroaryl, five- or six-membered, comprising one to three nitrogen atoms and/or a sulfur or oxygen atom, phenoxy or phenyl, it being possible for the aryl radicals mentioned in turn to be mono- to trisubstituted by halogen, hydroxyl, mercapto, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, NH($C_1$–$C_4$-alkyl) or N($C_1$–$C_4$-alkyl)$_2$;

phenyl or naphthyl, which in each case can be mono- to trisubstituted by: halogen, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, NH($C_1$–$C_4$-alkyl), N($C_1$–$C_4$-alkyl)$_2$, dioxomethylene or dioxoethylene;

a five- or six-membered heteroaromatic, comprising one to three nitrogen atoms and/or a sulfur or oxygen atom which can carry one to four halogen atoms and/or one to two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_3$–$C_8$-cycloalkyl, it being possible for these radicals in each case to be mono- to trisubstituted by: halogen, hydroxyl, mercapto, $C_1$–$C_4$-alkyl, $C_2$–$C_4$-alkenyl, $C_2$–$C_4$-alkynyl, $C_1$–$C_4$-alkoxy, $C_1$–$C_4$-alkylthio, $C_1$–$C_4$-haloalkoxy;

$R^9$ and $R^{10}$ (which can be identical or different) are:

hydrogen, halogen, $C_1$–$C_4$-alkoxy, $C_1$–$C_4$-haloalkoxy, $C_1$–$C_4$-alkylthio, $C_1$–$C_4$-alkylcarbonyl, $C_1$–$C_4$-alkoxycarbonyl, $NH_2$, NH($C_1$–$C_4$-alkyl), N($C_1$–$C_4$-alkyl)$_2$, hydroxyl;

$C_1$–$C_4$-alkyl, $C_2$–$C_4$-alkenyl, $C_2$–$C_4$-alkynyl, it being possible for these radicals to be substituted by halogen, hydroxyl, mercapto, cyano;

or $CR^9$ or $CR^{10}$ is linked to $CR^2$ as indicated under $R^2$ to give a 5- or 6-membered ring;

W is sulfur, oxygen or a single bond;

Q is oxygen or nitrogen, with the proviso that if Q=nitrogen then W is a single bond.

Particularly preferred compounds of the formula I, both as pure enantiomers and pure diastereomers or as a mixture thereof, are those in which the substituents have the following meanings:

X is nitrogen or methine; with the proviso that if X=nitrogen then Z=nitrogen and Y=$CR^9$ and if X=methine then Y=nitrogen and Z=$CR^{10}$ or Y=$CR^9$ and Z=nitrogen;

Y is nitrogen or $CR^9$;

Z is nitrogen or $CR^{10}$;

$R^2$ is $C_1$–$C_4$-alkyl, trifluoromethyl, hydrogen, fluorine, $C_1$–$C_4$-alkoxy, trifluoromethoxy, $C_1$–$C_4$-alkylthio;

or $CR^2$, together with $CR^9$ or $CR^{10}$, forms a 5- or 6-membered alkylene or alkenylene ring, which can be substituted by one or two $C_1$–$C_4$-alkyl groups, and where in each case one or more methylene groups can be replaced by oxygen or sulfur;

$R^3$ and $R^4$ (which can be identical or different) are:

phenyl or naphthyl, which can be substituted by one or more of the following radicals: halogen, cyano, $C_1$–$C_4$-alkyl, trifluoromethyl, $C_1$–$C_4$-alkoxy, trifluoromethoxy, $C_1$–$C_4$-alkylthio or phenyl, which can be mono- to trisubstituted by halogen, $C_1$–$C_4$-alkyl, trifluoromethyl, $C_1$–$C_4$-alkoxy or $C_1$–$C_4$-alkylthio; or phenyl or naphthyl, which are connected in the ortho position via a direct bond, a methylene, ethylene or ethenylene group;

$C_5$–$C_6$-cycloalkyl, it being possible for these radicals in each case to be mono- to trisubstituted by: halogen, $C_1$–$C_4$-alkyl, $C_1$–$C_4$-alkoxy, $C_1$–$C_4$-alkylthio;

$R^5$ is hydrogen, $C_1$–$C_8$-alkyl, $C_3$–$C_8$-alkenyl or $C_3$–$C_8$-alkynyl, it being possible for these radicals in each case to be mono- to trisubstituted by: halogen, hydroxyl, mercapto, carboxyl, cyano, amino, $C_1$–$C_4$-alkoxy, $C_1$–$C_4$-alkylthio, $C_1$–$C_4$-alkoxycarbonyl, $NH(C_1$–$C_4$-alkyl), $N(C_1$–$C_4$-alkyl)$_2$, $C_3$–$C_8$-cycloalkyl, heteroaryloxy or heteroaryl, five- or six-membered, comprising one to three nitrogen atoms and/or a sulfur or oxygen atom, phenoxy or phenyl, it being possible for the aryl radicals mentioned in turn to be mono- to trisubstituted by halogen, cyano, hydroxyl, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $N(C_1$–$C_4$-alkyl)$_2$;

phenyl or naphthyl, which in each case can be mono- to trisubstituted by: halogen, $C_1$–$C_4$-alkyl, trifluoromethyl, $C_1$–$C_4$-alkoxy, $C_1$–$C_4$-haloalkoxy, phenoxy, $C_1$–$C4_4$-alkylthio, dioxomethylene or dioxoethylene;

a five- or six-membered heteroaromatic, comprising one to three nitrogen atoms and/or a sulfur or oxygen atom, which can carry one to four halogen atoms and/or one to two of the following radicals: $C_1$–$C_4$-alkyl, trifluoromethyl, $C_1$–$C_4$-alkoxy, $C_1$–$C_4$-alkylthio, phenyl, phenoxy, it being possible for the phenyl radicals in turn to carry one to five halogen atoms and/or one to three of the following radicals: $C_1$–$C_4$-alkyl, $C_1$–$C_4$-alkoxy or $C_1$–$C_4$-alkylthio;

$C_3$–$C_8$-cycloalkyl, it being possible for these radicals in each case to be mono- to trisubstituted by: halogen, $C_1$–$C_4$-alkyl, $C_1$–$C_4$-alkoxy, $C_1$–$C_4$-alkylthio;

$R^9$ and $R^{10}$ (which can be identical or different) are:
trifluoromethyl, trifluoromethoxy, hydrogen, $C_1$–$C_4$-alkoxy, $C_1$–$C_4$-alkylthio, $NH(C_1$–$C_4$-alkyl), $N(C_1$–$C_4$-alkyl)$_2$, $C_1$–$C_4$-alkyl, vinyl;

or $CR^9$ or $CR^{10}$ is linked to $CR^2$ as indicated under $R^2$ to give a 5- or 6-membered ring;

W is sulfur, oxygen or a single bond;

Q is oxygen or nitrogen; with the proviso that if Q=nitrogen then W is a single bond.

SYNTHEIS EXAMPLES

For the synthesis of 2-hydroxy-3-methoxy-3,3-diphenylpropionic acid and 2-hydroxy-3,3-diphenylbutyric acid see WO 96/11914 and DE 19614533.3.

Example 1

2-(6-Methylpyridazin-3-yloxy)-3-methoxy-3,3-diphenylpropionic acid (I-517)

1.3 g (4.8 mmol) of 2-hydroxy-3-methoxy-3,3-diphenylpropionic acid dissolved in DMF were added dropwise to a suspension of 0.43 g of NaH (14.3 mmol, 80% in white oil) in 10 ml of DMF. After stirring to room temperature for 30 minutes, the mixture was treated with 0.6 g (4.8 mmol) of 3-chloro-6-methylpyridazine in 10 ml of DMF and stirred overnight at room temperature. To complete the reaction, 0.6 g (4.8 mmol) of 3-chloro-6-methylpyridazine were then added again and the mixture was kept at 60° C. for 5 hours. It was poured onto ice water, extracted three times with ethyl acetate, the aqueous phase was brought to pH 2 with half-concentrated hydrochloric acid and the precipitate which was deposited was extracted with ethyl acetate. These ethyl acetate phases were dried with magnesium sulfate and then filtered and the solvent was stripped off under reduced pressure. 800 mg of the brown residue (1.19 g) were purified by means of MPLC, it being possible to isolate 199 mg of the desired product as a white solid.

$^1$H—NMR (200 MHz, DMSO): 7.5 ppm (1 H, d), 7.2–7.3 (10 H, m), 7.1 (1 H, d), 6.3 (1 H, s), 3.3 (3 H, s), 2.5 (3 H, s).

FAB-MS: 365 (M+H$^+$)

Example 2

The following compounds were prepared similarly to Example 1:

2-(6-Methoxypyrazin-2-yloxy)-3-methoxy-3,3-diphenylpropionic acid (I-384)

$^1$H—NMR (200 MHz, DMSO): 7.9 ppm (1 H, s), 7.8 ppm (1 H, s), 7.2–7.3 (10 H, m), 6.1 (1 H, s), 3.9 (3 H, s), 3.3 (3 H, s).

FAB-MS: 380 (M+H$^+$)

2-(6-Methoxypyridazin-3-yloxy)-3,3-diphenylbutyric acid

1H—NMR (200 MHz, DMSO): 12.3–12.6 ppm (broad, 1 H), 7.0–7.4 (12 H, m), 6.0 (1 H, s), 3.9 (3 H, s), 1.8 (3 H, s).

FAB-MS: 365 (M+H$^+$)

The compounds listed in Table 1 can be prepared in a similar manner or as described in the general section.

TABLE I $$R^5-W-\underset{R^3}{\overset{R^4}{\underset{|}{C}}}-\underset{R^1}{\overset{|}{CH}}-Q-\underset{N=Z}{\overset{X-Y}{\diagup\diagdown}}-R^2$$

I

| No. | R¹ | R³, R⁴ | R⁵ | X | Y | R² | Z | Q | W |
|---|---|---|---|---|---|---|---|---|---|
| I-1 | COOH | phenyl | methyl | N | C-Me | Me | N | O | S |
| I-2 | COOH | 4-Cl-phenyl | methyl | N | C—OMe | Me | N | O | O |
| I-3 | COOH | phenyl | methyl | CH | N | Me | C-ethyl | O | — |
| I-4 | COOH | phenyl | methyl | CH | N | Me | C—SMe | O | — |
| I-5 | COOH | 4-F-phenyl | methyl | N | C-Me | OMe | N | O | O |
| I-6 | COOH | 4-F-phenyl | methyl | N | C-ethyl | Me | N | O | O |
| I-7 | COOH | 4-Cl-phenyl | methyl | N | C—OMe | H | N | O | O |
| I-8 | COOH | phenyl | 4-OMe-phenyl-(CH₂)₂— | N | C—CH₂—CH₂—CH₂ | N | O | O |
| I-9 | COOH | phenyl | 4-OMe-phenyl-(CH₂)₂— | N | C-Me | ethyl | N | O | O |
| I-10 | COOH | 4-Me-phenyl | methyl | N | C—O—CH₂—O | N | O | O |
| I-11 | COOMe | phenyl | methyl | N | C—O—CH₂—CH₂ | N | O | O |
| I-12 | COOH | phenyl | methyl | CH | N | Me | C—OMe | O | — |
| I-13 | COOH | phenyl | methyl | CH | N | OMe | C-Me | O | — |
| I-14 | COOH | cyclohexyl | methyl | CH | CH | Me | N | O | O |
| I-15 | COOH | phenyl | propyl | CH | CH | OMe | N | O | O |
| I-16 | COOH | phenyl | 2-cyclopropyleth-1-yl | CH | C-Me | Me | N | O | O |
| I-17 | COOH | phenyl | 4-OMe-phenyl-(CH₂)₂— | N | C-Me | Me | N | O | O |
| I-18 | COOH | phenyl | 4-OMe-phenyl-(CH₂)₂— | N | C—OMe | Me | N | O | O |
| I-19 | COOH | phenyl | cyclohexyl-(CH₂)₂— | CH | C—OMe | Me | N | O | O |
| I-20 | COOH | 4-F-phenyl | methyl | CH | C—OMe | OMe | N | O | O |
| I-21 | COOH | phenyl | methyl | CH | N | Me | CH | O | — |
| I-22 | COOH | phenyl | methyl | CH | N | Me | C-Me | O | — |
| I-23 | COOH | 4-F-phenyl | methyl | CH | C-Me | OMe | N | O | O |
| I-24 | COOH | phenyl | methyl | CH | C-Ethyl | Me | N | O | S |
| I-25 | COOH | phenyl | methyl | CH | C—OMe | H | N | O | S |
| I-26 | COOH | phenyl | 3,4-di-OMe-phenyl-(CH₂)₂— | CH | N | Me | C—CH₂—OH | O | O |
| I-27 | COOH | phenyl | 3,4-di-OMe-phenyl-(CH₂)₂— | CH | N | Me | C—N(CH₃)₂ | O | O |
| I-28 | tetrazole | phenyl | methyl | CH | C—O—CH₂—O | N | O | O |
| I-29 | COOH | 4-Me-phenyl | methyl | CH | C—O—CH₂—CH₂ | N | O | O |
| I-30 | COOH | phenyl | methyl | CH | C—N(CH₃)₂ | Me | N | O | — |
| I-31 | COOH | phenyl | methyl | CH | C—NH(CH₃) | OMe | N | O | — |
| I-32 | COOH | 4-F-phenyl | methyl | CH | C—OMe | CF₃ | N | O | O |
| I-33 | COOH | 4-Cl-phenyl | methyl | CH | C-Me | ethyl | N | O | O |
| I-34 | COOH | phenyl | methyl | CH | C-ethyl | CF₃ | N | O | O |
| I-35 | COOH | phenyl | 3,4-di-OMe-phenyl-(CH₂)₂— | CH | N | CH₂—CH₂—O—C | O | O |
| I-36 | COOH | phenyl | 3,4-di-OMe-phenyl-(CH₂)₂— | CH | N | F | C—OMe | O | O |
| I-37 | COOH | phenyl | propyl | CH | C—CH₂—OH | Me | N | O | O |
| I-38 | COOH | cyclohexyl | methyl | CH | C—N(CH₃)₂ | Me | N | O | O |
| I-39 | COOH | phenyl | methyl | CH | C-ethyl | F | N | O | — |
| I-40 | COOH | phenyl | methyl | CH | C—CH₂—OH | Me | N | O | — |
| I-41 | tetrazole | phenyl | methyl | CH | C—NH(CH₃) | OMe | N | O | O |
| I-42 | COOH | phenyl | cyclopentyl | CH | N | Me | CH | O | O |
| I-43 | COOH | phenyl | methyl | CH | N | H | C—OCF₃ | O | O |
| I-44 | COOH | phenyl | 3,4-di-OMe-phenyl-(CH₂)₂— | CH | N | Me | C-ethyl | O | O |
| I-45 | COOH | phenyl | 3,4-di-OMe-phenyl-(CH₂)₂— | CH | N | O—CH₂—CH₂—C | O | O |
| I-46 | COOH | phenyl | methyl | CH | N | Me | C-Me | O | S |
| I-47 | COOH | phenyl | methyl | CH | N | Me | C—OMe | O | S |
| I-48 | COOH | phenyl | methyl | CH | C-Me | F | N | O | — |
| I-49 | COOH | phenyl | methyl | CH | C—CH₂—CH₂—CH₂ | N | O | — |
| I-50 | COOH | 4-F-phenyl | methyl | CH | N | OMe | C—OMe | O | O |
| I-51 | COOH | 4-OMe-phenyl | methyl | CH | N | OMe | C-Me | O | O |
| I-52 | COOH | phenyl | methyl | CH | N | Me | C-ethyl | O | S |
| I-53 | COOH | phenyl | 3,4-di-OMe-phenyl-(CH₂)₂— | CH | N | Me | C—OMe | O | O |
| I-54 | COOH | phenyl | 3,4-di-OMe-phenyl-(CH₂)₂— | CH | N | F | C-Me | O | O |
| I-55 | COOH | phenyl | cyclopentyl-(CH₂)₂— | CH | N | H | C—OMe | O | O |
| I-56 | COOH | phenyl | methyl | CH | N | CH₂—CH₂—S—C | O | O |
| I-57 | COOH | phenyl | methyl | CH | C—O—CH₂—O | N | O | — |
| I-58 | COOH | phenyl | methyl | CH | C—O—CH₂—CH₂ | N | O | — |
| I-59 | COOH | 4-Br-phenyl | methyl | CH | N | CH₂—CH₂—CH₂—C | O | O |
| I-60 | COOMe | phenyl | methyl | CH | N | O—CH₂—CH₂—C | O | O |
| I-61 | COOH | 4-Me-phenyl | methyl | CH | N | CH₂—CH₂—O—C | O | O |
| I-62 | COOH | phenyl | 3,4-di-OMe-phenyl-(CH₂)₂— | CH | C—N(CH₃)₂ | Me | N | O | O |
| I-63 | COOH | phenyl | 3,4-di-OMe-phenyl-(CH₂)₂— | CH | N | Me | C-Me | O | O |
| I-64 | COOH | 3-Cl-phenyl | methyl | CH | N | F | C—OMe | O | O |
| I-65 | COOH | phenyl | 3,4-di-OMe-phenyl- | CH | N | ethyl | C-Me | O | O |
| I-66 | COOH | phenyl | methyl | CH | C-ethyl | Me | N | O | — |
| I-67 | COOH | phenyl | methyl | CH | C—OMe | H | N | O | — |
| I-68 | COOH | phenyl | 4-OMe-phenyl- | CH | N | OMe | C-ethyl | O | O |
| I-69 | COOH | phenyl | 4-Me-phenyl- | CH | N | Me | C—CH₂—OH | O | O |

TABLE I-continued

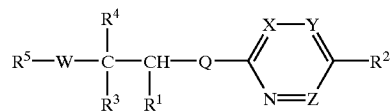

I

| No. | R¹ | R³, R⁴ | R⁵ | X | Y | R² | Z | Q | W |
|---|---|---|---|---|---|---|---|---|---|
| I-70 | COOH | 4-F-phenyl | methyl | CH | N | Me | C—N(CH₃)₂ | O | O |
| I-71 | COOH | phenyl | 3,4-di-OMe-phenyl-(CH₂)₂— | CH | C—O—CH₂—CH₂ | N | | O | O |
| I-72 | COOH | phenyl | 3,4-di-OMe-phenyl-(CH₂)₂— | CH | C—CH₂—OH | Me | N | O | O |
| I-73 | tetrazole | phenyl | methyl | CH | N | OMe | C—NH(CH₃) | O | O |
| I-74 | COOH | phenyl | 3,4-di-OMe-phenyl- | N | C-Me | Me | N | O | O |
| I-75 | COOH | phenyl | methyl | CH | C—OMe | OMe | N | O | — |
| I-76 | COOH | phenyl | methyl | CH | C—NH₂ | OMe | N | O | — |
| I-77 | COOH | phenyl | 3,4-di-OMe-phenyl- | N | C—OMe | Me | N | O | O |
| I-78 | COOH | phenyl | 4-OMe-phenyl- | N | C—CH₂—CH₂—CH₂ | N | | O | O |
| I-79 | COOH | phenyl | cyclopentyl-(CH₂)₂— | N | C-Me | OMe | N | O | O |
| I-80 | COOH | phenyl | 3,4-di-OMe-phenyl-(CH₂)₂— | CH | C—OMe | Me | N | O | O |
| I-81 | COOH | phenyl | 3,4-di-OMe-phenyl-(CH₂)₂— | CH | C—CH₂—CH₂—CH₂ | N | | O | O |
| I-82 | COOH | phenyl | cyclohexyl-(CH₂)₂— | N | C—O—CH₂—O | N | | O | O |
| I-83 | COOH | 4-F-phenyl | ethyl | CH | C—NH(CH₃) | Me | N | O | O |
| I-84 | COOH | phenyl | methyl | CH | C-Me | Me | N | O | — |
| I-85 | COOH | phenyl | methyl | CH | C—OMe | Me | N | O | — |
| I-86 | COOH | cyclohexyl | propyl | CH | C-Me | Me | N | O | O |
| I-87 | COOH | 4-Cl-phenyl | i-propyl | CH | C—OMe | Me | N | O | O |
| I-88 | COOH | 4-F-phenyl | ethyl | CH | C—OMe | NH₂ | N | O | O |
| I-89 | COOH | phenyl | 3,4-di-OMe-phenyl-(CH₂)₂— | CH | C—NH(CH₃) | Me | N | O | O |
| I-90 | COOH | phenyl | 3,4-di-OMe-phenyl-(CH₂)₂— | CH | C-Me | Me | N | O | O |
| I-91 | COOH | phenyl | ethyl | CH | C-ethyl | ethyl | N | O | S |
| I-92 | COOH | phenyl | ethyl | CH | C—CH₂—CH₂—CH₂ | N | | O | S |
| I-93 | COOH | phenyl | methyl | CH | CH | Me | N | O | — |
| I-94 | COOH | phenyl | methyl | CH | C—N(CH₃)₂ | Me | N | O | — |
| I-95 | COOH | phenyl | ethyl | CH | C—O—CH₂—CH₂ | N | | O | S |
| I-96 | COOH | phenyl | ethyl | CH | C-Me | F | N | O | S |
| I-97 | COOH | 4-Me-phenyl | ethyl | CH | C—CH₂—OH | Me | N | O | O |
| I-98 | COOH | phenyl | 3,4-di-OMe-phenyl-(CH₂)₂— | N | C-Me | OMe | N | O | O |
| I-99 | COOH | phenyl | 3,4-di-OMe-phenyl-(CH₂)₂— | N | C—O—CH₂—O | N | | O | O |
| I-100 | COOH | 4-OCF₃-phenyl | ethyl | CH | C—N(CH₃)₂ | Me | N | O | O |
| I-101 | COOH | phenyl | propyl | CH | N | Me | CH | O | O |
| I-102 | COOH | phenyl | methyl | N | C—O—CH₂—O | N | | O | — |
| I-103 | COOH | phenyl | methyl | N | C—O—CH₂—CH₂ | N | | O | — |
| I-104 | COOEt | phenyl | ethyl | CH | N | OMe | CH | O | O |
| I-105 | COOH | 4-Et-phenyl | ethyl | CH | N | Me | C-Me | O | O |
| I-106 | COOH | phenyl | 4-i-propyl-phenyl- | CH | N | Me | C—OMe | O | O |
| I-107 | COOH | phenyl | 3,4-di-OMe-phenyl-(CH₂)₂— | N | C—OMe | Me | N | O | O |
| I-108 | COOH | phenyl | 3,4-di-OMe-phenyl-(CH₂)₂— | N | C—CH₂—CH₂—CH₂ | N | | O | O |
| I-109 | COOH | phenyl | 4-i-propyl-phenyl-(CH₂)₂— | CH | N | ethyl | C-Me | O | O |
| I-110 | COOH | phenyl | 3,4-di-Me-phenyl-(CH₂)₂— | CH | N | Me | C-ethyl | O | O |
| I-111 | COOH | phenyl | methyl | N | C-ethyl | Me | N | O | — |
| I-112 | COOH | phenyl | methyl | N | C—OMe | H | N | O | — |
| I-113 | COOH | phenyl | 3,4-di-Me-phenyl-(CH₂)₂— | CH | N | O—CH₂—CH₂—C | | O | O |
| I-114 | COOH | phenyl | 4-SMe-phenyl-(CH₂)₂— | CH | N | CH₂—CH₂—O—C | | O | O |
| I-115 | COOH | 4-F-phenyl | ethyl | CH | N | F | C—OMe | O | O |
| I-116 | COOH | phenyl | HO—CH₂—CH₂— | CH | N | OMe | C-ethyl | O | O |
| I-117 | COOH | phenyl | 3,4-di-OMe-phenyl-(CH₂)₂— | N | C-Me | Me | N | O | O |
| I-118 | COOH | phenyl | 3-hexen-1-yl | CH | N | OMe | C-ethyl | O | O |
| I-119 | COOH | phenyl | 3-hepten-1-yl | CH | N | Me | C—CH₂—OH | O | O |
| I-120 | COOH | phenyl | methyl | N | C—OMe | Me | N | O | — |
| I-121 | COOH | phenyl | methyl | N | C—CH₂—CH₂—CH₂ | N | | O | — |
| I-122 | COOH | 4-Cl-phenyl | ethyl | CH | N | Me | C—N(CH₃)₂ | O | O |
| I-123 | COOH | phenyl | HO—CH₂—(CH—OH)—CH₂— | N | C-Me | Me | N | O | O |
| I-124 | COOH | phenyl | HO—CH₂—(CH—OH)—CH₂— | N | C—OMe | Me | N | O | O |
| I-125 | COOH | phenyl | HO—CH₂—CH₂— | CH | N | CH₂—CH₂—CH₂—C | | O | O |
| I-126 | COOH | phenyl | HO—CH₂—CH₂— | CH | N | F | C—OMe | O | O |
| I-127 | COOH | phenyl | HO—CH₂—(CH—OH)—CH₂— | N | C—CH₂—CH₂ | N | | O | O |
| I-128 | COOH | phenyl | phenyl-O—(CH₂)₂— | CH | C-Me | Me | N | O | O |
| I-129 | COOH | phenyl | ethyl | CH | N | Me | C—N(CH₃)₂ | N | — |
| I-130 | COOH | phenyl | methyl | N | C-Me | Me | N | O | — |
| I-131 | COOH | phenyl | 4-OMe-phenyl-O—(CH₂)₂— | CH | C—OMe | Me | N | O | O |
| I-132 | COOH | 4-F-phenyl | HO—CH₂—CH₂— | CH | C-Ethyl | ethyl | N | O | O |
| I-133 | COOH | phenyl | HO—CH₂—CH₂— | CH | C—CH₂—CH₂—S | N | | O | O |
| I-134 | COOH | phenyl | HO—CH₂—CH₂— | CH | N | ethyl | C-Me | O | O |
| I-135 | COOH | phenyl | HO—CH₂—CH₂— | CH | N | Me | C-ethyl | O | O |
| I-136 | COOMe | phenyl | HO—CH₂—CH₂— | CH | C—O—CH₂—CH₂ | N | | O | O |
| I-137 | COOH | 4-F-phenyl | HO—CH₂—CH₂— | CH | C-Me | F | N | O | O |
| I-138 | COOH | phenyl | ethyl | CH | N | O—CH₂—O—C | | N | — |

TABLE I-continued

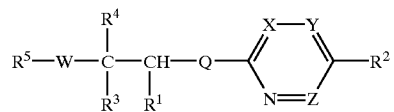

| No. | R$^1$ | R$^3$, R$^4$ | R$^5$ | X | Y | R$^2$ | Z | Q | W |
|---|---|---|---|---|---|---|---|---|---|
| I-139 | COOH | phenyl | ethyl | CH | N | CH$_2$—CH$_2$—CH$_2$—C | N | — |
| I-140 | COOH | 4-F-phenyl | HO—CH$_2$—CH$_2$— | CH | C—CH$_2$—OH | Me | N | O | O |
| I-141 | COOH | phenyl | HO—CH$_2$—CH$_2$—CH$_2$— | CH | N | Me | C-Me | O | O |
| I-142 | COOH | phenyl | HO—CH$_2$—CH$_2$—CH$_2$— | CH | N | Me | C—OMe | O | O |
| I-143 | COOH | phenyl | HO—CH$_2$—CH$_2$— | CH | N | Me | C-Me | O | O |
| I-144 | COOH | phenyl | HO—CH$_2$—CH$_2$— | CH | N | Me | C—OMe | O | O |
| I-145 | COOH | 4-Br-phenyl | HO—CH$_2$—CH$_2$— | CH | N | ethyl | C-Me | O | O |
| I-146 | COOH | 4-Me-phenyl | HO—CH$_2$—CH$_2$— | CH | N | Me | C-ethyl | O | O |
| I-147 | COOH | phenyl | ethyl | CH | N | OMe | C-Me | N | — |
| I-148 | COOH | phenyl | ethyl | CH | N | Me | C-ethyl | N | — |
| I-149 | COOH | 2-Me-phenyl | HO—CH$_2$—CH$_2$— | CH | N | CH$_2$—CH$_2$—C | O | O |
| I-150 | COOH | 2-Me-phenyl | HO—CH$_2$—CH$_2$—CH$_2$— | CH | N | F | C—OMe | O | O |
| I-151 | COOH | phenyl | HO—CH$_2$—(CH—OH)—CH$_2$— | CH | N | OMe | C-ethyl | O | O |
| I-152 | COOH | phenyl | HO—CH$_2$—CH$_2$— | CH | C-Me | F | N | O | O |
| I-153 | COOH | phenyl | HO—CH$_2$—CH$_2$— | CH | C—CH$_2$—OH | Me | N | O | O |
| I-154 | COOH | phenyl | 3,4,5-tri-OMe-phenyl-(CH$_2$)$_2$— | N | C-Me | Me | N | O | O |
| I-155 | COOH | phenyl | 3,4,5-tri-OMe-phenyl-(CH$_2$)$_2$— | N | C—OMe | Me | N | O | O |
| I-156 | COOH | phenyl | ethyl | CH | N | Me | C-Me | N | — |
| I-157 | COOH | phenyl | ethyl | CH | N | Me | C—OMe | N | — |
| I-158 | COOH | phenyl | 3,4-di-Cl-phenyl-(CH$_2$)$_2$— | N | C—CH$_2$—CH$_2$—CH$_2$ | N | O | O |
| I-159 | COOH | phenyl | 4-Cl-phenyl-(CH$_2$)$_2$— | N | C-Me | OMe | N | O | O |
| I-160 | COOH | phenyl | 3,4-di-Cl-phenyl-(CH$_2$)$_2$— | N | C—O—CH$_2$—O | N | O | O |
| I-161 | COOH | phenyl | HO—CH$_2$—CH$_2$— | CH | C—CH$_2$—CH$_2$—CH$_2$ | N | O | O |
| I-162 | COOH | phenyl | HO—CH$_2$—CH$_2$— | CH | C—O—CH$_2$—CH$_2$ | N | O | O |
| I-163 | COOH | phenyl | 3,4-di-OMe-phenyl-(CH$_2$)$_3$— | CH | C—NH(CH$_3$) | Me | N | O | O |
| I-164 | COOH | 4-F-phenyl | 3,4-di-OMe-phenyl-(CH$_2$)$_2$— | CH | C-Me | Me | N | O | O |
| I-165 | COOH | phenyl | ethyl | CH | C-Me | ethyl | N | N | — |
| I-166 | COOH | phenyl | ethyl | CH | C-ethyl | OMe | N | N | — |
| I-167 | COOH | phenyl | 3,4,5-tri-OMe-phenyl-(CH$_2$)$_2$— | CH | C—OMe | Me | N | O | O |
| I-168 | COOH | 4-Cl-phenyl | 3,4-di-OMe-phenyl-(CH$_2$)$_2$— | CH | C—CH$_2$—CH$_2$—CH$_2$ | N | O | O |
| I-169 | COOH | phenyl | 3,4-di-OMe-phenyl-(CH$_2$)$_3$— | CH | C—O—CH$_2$—CH$_2$ | N | O | O |
| I-170 | COOH | phenyl | HO—CH$_2$—CH$_2$— | CH | C—OMe | Me | N | O | O |
| I-171 | COOH | phenyl | HO—CH$_2$—CH$_2$— | CH | C-ethyl | ethyl | N | O | O |
| I-172 | COOH | phenyl | 4-Br-phenyl-(CH$_2$)$_2$— | CH | C—CH$_2$—OH | Me | N | O | O |
| I-173 | COOH | phenyl | 3,4-di-Me-phenyl-(CH$_2$)$_2$— | CH | C—N(CH$_3$)$_2$ | Me | N | O | O |
| I-174 | COOH | phenyl | ethyl | CH | C—CH$_2$—CH$_2$—CH$_2$ | N | N | — |
| I-175 | COOH | phenyl | ethyl | CH | C—O—CH$_2$—CH$_2$ | N | N | — |
| I-176 | COOH | phenyl | 3,4-di-Me-phenyl-(CH$_2$)$_2$— | CH | N | Me | C-Me | O | O |
| I-177 | COOH | phenyl | 3,4-di-OMe-phenyl-(CH$_2$)$_2$— | CH | N | Me | C—OMe | O | S |
| I-178 | COOH | phenyl | 3,4-di-OMe-phenyl-(CH$_2$)$_2$— | CH | N | F | C-Me | O | S |
| I-179 | COOH | phenyl | HO—CH$_2$—CH$_2$— | N | C—CH$_2$—CH$_2$—CH$_2$ | N | O | O |
| I-180 | COOH | phenyl | HO—CH$_2$—CH$_2$— | CH | C-Me | Me | N | O | O |
| I-181 | COOH | phenyl | 3,4-di-OMe-phenyl-(CH$_2$)$_2$— | CH | N | Me | C-ethyl | O | S |
| I-182 | COOH | 4-F-phenyl | 3,4-di-OMe-phenyl-(CH$_2$)$_2$— | CH | N | O—CH$_2$—CH$_2$—C | O | O |
| I-183 | COOH | phenyl | ethyl | CH | C-Me | Me | N | N | — |
| I-184 | COOH | phenyl | ethyl | CH | C—OMe | Me | N | N | — |
| I-185 | COOH | 4-F-phenyl | 3,4-di-OMe-phenyl-(CH$_2$)$_2$— | CH | N | CH$_2$—CH$_2$—O—C | O | O |
| I-186 | COOH | phenyl | 3,4-di-Cl-phenyl-(CH$_2$)$_2$— | CH | N | F | C—OMe | O | O |
| I-187 | COOH | phenyl | 4-Cl-phenyl-(CH$_2$)$_2$— | CH | N | Me | C—CH$_2$—OH | O | O |
| I-188 | COOH | phenyl | HO—CH$_2$—CH$_2$— | N | C-Me | Me | N | O | O |
| I-189 | COOH | phenyl | HO—CH$_2$—CH$_2$— | N | C—OMe | Me | N | O | O |
| I-190 | COOH | 4-Cl-phenyl | 3,4-di-OMe-phenyl-(CH$_2$)$_2$— | CH | N | Me | C—N(CH$_3$)$_2$ | O | O |
| I-191 | COOH | Phenyl | 4-i-propyl-phenyl-(CH$_2$)$_2$— | N | C-Me | Me | N | O | O |
| I-192 | COOH | phenyl | ethyl | N | C-ethyl | Me | N | N | — |
| I-193 | COOH | phenyl | ethyl | N | C—O—CH$_2$—CH$_2$ | N | N | — |
| I-194 | COOH | phenyl | 4-i-propyl-phenyl-(CH$_2$)$_2$— | N | C—OMe | Me | N | O | O |
| I-195 | COOH | phenyl | 4-ethyl-phenyl-(CH$_2$)$_2$— | N | C—CH$_2$—CH$_2$—CH$_2$ | N | O | O |
| I-196 | COOH | phenyl | 4-OMe-phenyl-(CH$_2$)$_2$— | N | C-Me | ethyl | N | O | S |
| I-197 | COOH | phenyl | ethyl | CH | N | Me | C—CH$_2$—OH | O | O |
| I-198 | COOH | phenyl | ethyl | CH | N | Me | C—N(CH$_3$)$_2$ | O | O |
| I-199 | COOH | phenyl | 4-ethyl-phenyl-(CH$_2$)$_2$— | N | C—O—CH$_2$—O | N | O | O |
| I-200 | COOH | 4-F-phenyl | 4-OMe-phenyl-(CH$_2$)$_2$— | CH | C—NH(CH$_3$) | Me | N | O | O |
| I-201 | COOH | phenyl | ethyl | N | C-Me | Me | N | N | — |
| I-202 | COOH | phenyl | ethyl | N | C—OMe | Me | N | N | — |
| I-203 | COOH | phenyl | 4-Br-phenyl-(CH$_2$)$_2$— | CH | C-Me | Me | N | O | O |
| I-204 | COOH | phenyl | 4-i-propyl-phenyl-(CH$_2$)$_2$— | CH | C—OMe | Me | N | O | O |
| I-205 | COOH | phenyl | 4-ethyl-phenyl-(CH$_2$)$_2$— | CH | C—CH$_2$—CH$_2$—CH$_2$ | N | O | S |
| I-206 | COOH | phenyl | ethyl | CH | N | F | C—OMe | O | O |
| I-207 | COOH | phenyl | ethyl | CH | N | OMe | C-ethyl | O | O |

TABLE I-continued

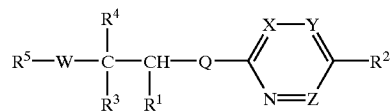

I

| No. | R¹ | R³, R⁴ | R⁵ | X | Y | R² | Z | Q | W |
|---|---|---|---|---|---|---|---|---|---|
| I-208 | COOH | 4-Cl-phenyl | 4-OMe-phenyl-(CH₂)₂— | CH | C—O—CH₂—CH₂ | | N | O | O |
| I-209 | COOH | 4-Me-phenyl | 4-OMe-phenyl-(CH₂)₂— | CH | C—CH₂—OH | Me | N | O | O |
| I-210 | COOH | phenyl | methyl | CH | N | OMe | C-ethyl | N | — |
| I-211 | COOH | phenyl | methyl | CH | N | Me | C—N(CH₃)₂ | N | — |
| I-212 | COOH | phenyl | 4-OMe-phenyl-(CH₂)₂— | CH | C—N(CH₃)₂ | Me | N | O | S |
| I-213 | COOH | phenyl | 4-propyl-phenyl-(CH₂)₂— | CH | N | Me | C-Me | O | O |
| I-214 | COOH | phenyl | 3,5-di-OMe-phenyl-(CH₂)₂— | CH | N | Me | C—OMe | O | O |
| I-215 | COOH | phenyl | ethyl | CH | N | O—CH₂—CH₂—C | | O | O |
| I-216 | COOH | phenyl | ethyl | CH | N | CH₂—CH₂—O—C | | O | O |
| I-217 | COOH | phenyl | 3,5-di-OMe-phenyl-(CH₂)₂— | CH | N | F | C-Me | O | O |
| I-218 | COOH | phenyl | 3,5-di-OMe-phenyl-(CH₂)₂— | CH | N | Me | C-ethyl | O | O |
| I-219 | COOH | phenyl | methyl | CH | N | O—CH₂—CH₂—C | | N | — |
| I-220 | COOH | phenyl | methyl | CH | N | CH₂—CH₂—O—C | | N | — |
| I-221 | COOH | phenyl | 3,5-di-OMe-phenyl-(CH₂)₂— | CH | N | CH₂—CH₂—CH₂—C | | O | O |
| I-222 | COOH | phenyl | 3,5-di-OMe-phenyl-(CH₂)₂— | CH | N | O—CH₂—CH₂—C | | O | O |
| I-223 | COOH | phenyl | 4-OMe-phenyl-(CH₂)₂— | CH | N | F | C—OMe | O | S |
| I-224 | COOH | phenyl | ethyl | CH | N | ethyl | C-Me | O | O |
| I-225 | COOH | phenyl | ethyl | CH | N | Me | C-ethyl | O | O |
| I-226 | COOH | phenyl | 4-propyl-phenyl-(CH₂)₂— | CH | N | Me | C—CH₂—OH | O | O |
| I-227 | COOH | phenyl | 4-N(CH₃)₂-phenyl-(CH₂)₂— | CH | N | Me | C—N(CH₃)₂ | O | O |
| I-228 | COOH | phenyl | methyl | CH | N | O—CH₂—O—C | | N | — |
| I-229 | COOH | phenyl | methyl | CH | N | CH₂—CH₂—CH₂—C | | N | — |
| I-230 | COOH | phenyl | 4-Cl-phenyl-CH₂— | N | C-Me | Me | N | O | O |
| I-231 | COOH | phenyl | 4-Me-phenyl-CH₂— | N | C—OMe | Me | N | O | O |
| I-232 | COOH | phenyl | 3,4-di-Me-phenyl-CH₂— | N | C—CH₂—CH₂—CH₂ | | N | O | O |
| I-233 | COOH | phenyl | ethyl | CH | N | Me | C-Me | O | O |
| I-234 | COOH | phenyl | ethyl | CH | N | Me | C—OMe | O | O |
| I-235 | COOH | phenyl | 4-OMe-phenyl-CH₂— | N | C-Me | ethyl | N | O | S |
| I-236 | COOH | 4-F-Phenyl | 4-OMe-phenyl-CH₂— | N | C—O—CH₂—O | | N | O | O |
| I-237 | COOH | phenyl | methyl | CH | N | OMe | C-Me | N | — |
| I-238 | COOH | phenyl | methyl | CH | N | Me | C-ethyl | N | — |
| I-239 | COOH | 4-F-phenyl | 4-OMe-phenyl-CH₂— | CH | Cl | Me | N | O | O |
| I-240 | COOH | phenyl | 4-OMe-phenyl-CH₂— | CH | C-Me | Me | N | O | S |
| I-241 | COOH | phenyl | 4-OMe-phenyl-CH₂— | CH | C—OMe | Me | N | O | S |
| I-242 | COOH | phenyl | ethyl | CH | N | Me | CH | O | O |
| I-243 | COOH | phenyl | ethyl | CH | N | OMe | CH | O | O |
| I-244 | COOH | phenyl | 4-Cl-phenyl-CH₂— | CH | C—CH₂—CH₂—CH₂ | | N | O | O |
| I-245 | COOH | phenyl | 4-Cl-phenyl-CH₂— | CH | C—O—CH₂—CH₂ | | N | O | O |
| I-246 | COOH | phenyl | methyl | CH | N | Me | C-Me | N | — |
| I-247 | COOH | phenyl | methyl | CH | N | Me | C—OMe | N | — |
| I-248 | COOH | 4-Cl-phenyl | 4-OMe-phenyl-CH₂— | CH | C—CH₂—OH | Me | N | O | O |
| I-249 | COOH | phenyl | HO—CH₂— | CH | N | Me | C—N(CH₃)₂ | O | — |
| I-250 | COOH | 4-Cl-phenyl | 4-OMe-phenyl-CH₂— | CH | C—N(CH₃)₂ | Me | N | O | O |
| I-251 | COOH | phenyl | 4-OMe-phenyl-CH₂— | CH | N | CF₃ | C-Me | O | O |
| I-252 | COOH | phenyl | ethyl | CH | C—CH₂—OH | Me | N | O | O |
| I-253 | COOH | phenyl | ethyl | CH | C—N(CH₃)₂ | Me | N | O | O |
| I-254 | COOH | phenyl | 4-OMe-phenyl-CH₂— | CH | N | CF₃ | C—OMe | O | O |
| I-255 | COOH | phenyl | 4-Br-phenyl-CH₂— | CH | N | F | C-Me | O | O |
| I-256 | COOH | phenyl | methyl | CH | C-Ethyl | OMe | N | N | — |
| I-257 | COOH | phenyl | methyl | CH | C—N(CH₃)₂ | Me | N | N | — |
| I-258 | COOH | phenyl | 4-i-propyl-phenyl-CH₂— | CH | N | Me | C-ethyl | O | O |
| I-259 | COOH | phenyl | HO—CH₂— | CH | N | CH₂—CH₂—CH₂—C | | O | — |
| I-260 | COOH | phenyl | HO—CH₂— | CH | N | OMe | C-ethyl | O | — |
| I-261 | COOH | phenyl | 4-ethyl-phenyl-CH₂— | CH | N | CH₂—CH₂—CH₂—C | | O | O |
| I-262 | COOH | phenyl | 4-i-propyl-phenyl-CH₂— | CH | N | O—CH₂—CH₂—C | | O | O |
| I-263 | COOH | phenyl | ethyl | CH | C—O—CH₂—CH₂ | | N | O | O |
| I-264 | COOH | phenyl | ethyl | CH | C-Me | F | N | O | O |
| I-265 | COOH | phenyl | 4-phenyl-phenyl-CH₂— | CH | N | F | C—OMe | O | O |
| I-266 | COOH | 4-F-phenyl | 4-OMe-phenyl-CH₂— | CH | N | Me | C—CH₂—OH | O | O |
| I-267 | COOH | phenyl | methyl | CH | C—OMe | F | N | N | — |
| I-268 | COOH | phenyl | methyl | CH | C-Me | ethyl | N | N | — |
| I-269 | COOH | 4-F-phenyl | 4-OMe-phenyl-CH₂— | CH | N | Me | C—N(CH₃)₂ | O | O |
| I-270 | COOH | phenyl | HO—CH₂— | CH | N | Me | C-ethyl | O | — |
| I-271 | COOH | phenyl | HO—CH₂— | CH | N | O—CH₂—O—C | | O | — |
| I-272 | COOH | phenyl | methyl | N | C-Me | CF₃ | N | N | — |
| I-273 | COOH | 4-OMe-phenyl | methyl | N | C—OMe | Me | N | N | — |
| I-274 | COOH | phenyl | ethyl | CH | C-ethyl | ethyl | N | O | O |
| I-275 | COOH | phenyl | ethyl | CH | C—CH₂—CH₂—CH₂ | | N | O | O |
| I-276 | COOH | 4-Me-phenyl | methyl | N | C-Me | OMe | N | N | — |

TABLE I-continued $$R^5-W-\underset{\underset{R^3}{|}}{\overset{\overset{R^4}{|}}{C}}-\underset{\underset{R^1}{|}}{CH}-Q-\underset{N=Z}{\overset{X-Y}{\diagup}}R^2$$

| No. | R¹ | R³, R⁴ | R⁵ | X | Y | R² | Z | Q | W |
|---|---|---|---|---|---|---|---|---|---|
| I-277 | COOH | 4-OMe-phenyl | methyl | N | C-ethyl | Me | N | N | — |
| I-278 | COOH | phenyl | methyl | CH | C—O—CH₂—O | N | N | — |
| I-279 | COOH | phenyl | methyl | CH | C—O—CH₂—CH₂ | N | N | — |
| I-280 | COOH | phenyl | 4-OMe-phenyl-CH₂— | N | C—O—CH₂—O | N | N | — |
| I-281 | COOH | phenyl | HO—CH₂— | CH | N | Me | C—OMe | O | O |
| I-282 | COOH | phenyl | HO—CH₂— | CH | N | OMe | C-Me | O | O |
| I-283 | COOH | phenyl | 4-OMe-phenyl-CH₂— | N | C—O—CH₂—CH₂ | N | N | — |
| I-284 | COOH | phenyl | phenyl-O—CH₂— | CH | C-Me | Me | N | N | — |
| I-285 | COOH | phenyl | ethyl | CH | C—OMe | Me | N | O | O |
| I-286 | COOH | phenyl | ethyl | CH | C—OMe | NH₂ | N | O | O |
| I-287 | COOH | phenyl | 3,4-di-OMe-phenyl-CH₂— | CH | C—OMe | Me | N | N | — |
| I-288 | COOH | phenyl | 3,4-di-OMe-phenyl-CH₂— | CH | C-Me | OMe | N | N | — |
| I-289 | COOH | phenyl | methyl | CH | C-Me | OMe | N | N | — |
| I-290 | COOH | phenyl | methyl | CH | C-ethyl | Me | N | N | — |
| I-291 | COOH | phenyl | phenyl-CH₂—O—CH₂— | CH | C-ethyl | Me | N | N | — |
| I-292 | COOH | phenyl | HO—CH₂— | CH | C—CH₂—CH₂—CH₂ | N | O | O |
| I-293 | COOH | phenyl | HO—CH₂— | CH | N | Me | C-Me | O | O |
| I-294 | COOH | phenyl | HO—CH₂— | CH | C—O—CH₂—O | N | N | — |
| I-295 | COOH | phenyl | HO—CH₂— | CH | C—O—CH₂—CH₂ | N | N | — |
| I-296 | COOH | phenyl | ethyl | CH | C—NH(CH₃) | Me | N | O | O |
| I-297 | COOH | phenyl | ethyl | CH | C-Me | Me | N | O | O |
| I-298 | COOH | phenyl | methyl | CH | C—OMe | CF₃ | N | N | — |
| I-299 | COOH | phenyl | 3,4-di-Me-phenyl-CH₂— | CH | C-Me | ethyl | N | N | — |
| I-300 | COOH | phenyl | methyl | CH | C-Me | Me | N | N | — |
| I-301 | COOH | phenyl | methyl | CH | C—OMe | Me | N | N | — |
| I-302 | COOH | 4-Me-phenyl | methyl | CH | C-ethyl | OMe | N | N | — |
| I-303 | COOH | phenyl | HO—CH₂— | CH | C—OMe | H | N | O | O |
| I-304 | COOH | phenyl | HO—CH₂— | CH | C—O—CH₂—CH₂ | N | O | O |
| I-305 | COOH | 4-OMe-phenyl | methyl | CH | C—N(CH₃)₂ | Me | N | N | — |
| I-306 | COOH | phenyl | methyl | CH | N | CF₃ | C-Me | N | — |
| I-307 | COOH | phenyl | ethyl | N | C-Me | OMe | N | O | O |
| I-308 | COOH | phenyl | ethyl | N | C—O—CH₂—O | N | O | O |
| I-309 | COOH | phenyl | 4-OMe-phenyl-CH₂— | CH | N | Me | C—OMe | N | — |
| I-310 | COOH | phenyl | HO—CH₂— | CH | N | OMe | C-Me | O | O |
| I-311 | COOH | phenyl | methyl | N | C—O—CH₂—O | N | N | — |
| I-312 | COOH | phenyl | methyl | N | C—O—CH₂—CH₂ | N | N | — |
| I-313 | COOH | phenyl | 4-Me-phenyl-CH₂— | CH | N | Me | C-ethyl | N | — |
| I-314 | COOH | phenyl | HO—CH₂— | CH | C—OMe | Me | N | O | O |
| I-315 | COOH | phenyl | HO—CH₂— | CH | C-ethyl | Me | N | O | O |
| I-316 | COOH | phenyl | 4-Me-phenyl-CH₂— | CH | N | O—CH₂—O—C | N | — |
| I-317 | COOMe | phenyl | methyl | CH | N | CH₂—CH₂—CH₂—C | N | — |
| I-318 | COOH | phenyl | ethyl | N | C—OMe | Me | N | O | O |
| I-319 | COOH | phenyl | ethyl | N | C—CH₂—CH₂—CH₂ | N | O | O |
| I-320 | COOH | 4-OMe-phenyl | methyl | CH | N | O—CH₂—CH₂—C | N | — |
| I-321 | COOH | 4-Me-phenyl | methyl | CH | N | CH₂—CH₂—O—C | N | — |
| I-322 | COOH | phenyl | methyl | N | C-Me | OMe | N | N | — |
| I-323 | COOH | phenyl | methyl | N | C-ethyl | Me | N | N | — |
| I-324 | COOH | phenyl | 4-OMe-phenyl-CH₂— | CH | N | OMe | C-ethyl | N | — |
| I-325 | COOH | phenyl | HO—CH₂— | N | C-ethyl | Me | N | N | — |
| I-326 | COOH | phenyl | HO—CH₂— | CH | C-Me | Me | N | O | — |
| I-327 | COOH | phenyl | 3,4-di-OMe-phenyl-CH₂— | CH | N | Me | C—N(CH₃)₂ | N | — |
| I-328 | COOH | phenyl | 4-OMe-phenyl-(CH₂)₂— | N | C-Me | Me | N | N | — |
| I-329 | COOH | phenyl | methyl | CH | N | OMe | C—NH(CH₃) | O | O |
| I-330 | COOH | phenyl | ethyl | N | C-Me | Me | N | O | O |
| I-331 | COOH | phenyl | 4-OMe-phenyl-(CH₂)₂— | N | C—OMe | Me | N | N | — |
| I-332 | COOH | phenyl | ethyl | N | C-ethyl | CF₃ | N | N | — |
| I-333 | COOH | phenyl | methyl | N | C-Me | Me | N | N | — |
| I-334 | COOH | phenyl | methyl | N | C—OMe | Me | N | N | — |
| I-335 | COOH | phenyl | HO—CH₂—CH₂— | N | C—O—CH₂—CH₂ | N | N | — |
| I-336 | COOH | phenyl | HO—CH₂— | N | C—OMe | Me | N | O | — |
| I-337 | COOH | phenyl | HO—CH₂— | N | C—CH₂—CH₂—CH₂ | N | O | — |
| I-338 | COOH | phenyl | HO—CH₂—CH₂— | CH | C-Me | Me | N | N | — |
| I-339 | COOH | phenyl | phenyl-CH₂—O—(CH₂)₂— | CH | C—OMe | Me | N | N | — |
| I-340 | COOH | phenyl | methyl | CH | N | Me | C—CH₂—OH | O | O |
| I-341 | COOH | phenyl | methyl | CH | N | Me | C—N(CH₃)₂ | O | O |
| I-342 | COOH | phenyl | phenyl-O—(CH₂)₂— | CH | C—CH₂—CH₂—CH₂ | N | N | — |
| I-343 | COOH | phenyl | 3,4-di-OMe-phenyl-O—(CH₂)₂— | CH | C—O—CH₂—CH₂ | N | N | — |
| I-344 | COOH | phenyl | 4-OMe-phenyl-CH₂— | CH | N | Me | C—CH₂—OH | O | O |
| I-345 | COOH | phenyl | 4-OMe-phenyl-CH₂— | CH | N | Me | C—N(CH₃)₂ | O | O |

TABLE I-continued

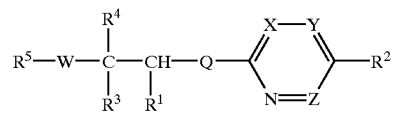

| No. | R¹ | R³, R⁴ | R⁵ | X | Y | R² | Z | Q | W |
|---|---|---|---|---|---|---|---|---|---|
| I-346 | COOH | phenyl | 3,4-di-OMe-phenyl-O—(CH₂)₂— | CH | C-Me | ethyl | N | N | — |
| I-347 | COOH | phenyl | ethyl | CH | N | OMe | C—NH(CH₃) | O | — |
| I-348 | COOH | phenyl | HO—CH₂— | N | C-Me | Me | N | O | — |
| I-349 | COOH | phenyl | HO—CH₂—CH₂— | CH | C-ethyl | OMe | N | N | — |
| I-350 | COOH | phenyl | propyl | CH | N | Me | C-Me | N | — |
| I-351 | COOH | phenyl | methyl | CH | N | Ethyl | C-Me | O | O |
| I-352 | COOH | phenyl | methyl | CH | N | OMe | C-ethyl | O | O |
| I-353 | COOH | phenyl | 3,4-di-OMe-phenyl-(CH₂)₃— | CH | N | Me | C—OMe | N | — |
| I-354 | COOH | phenyl | 3,4-di-OMe-phenyl-(CH₂)₃— | CH | N | OMe | C-Me | N | — |
| I-355 | COOH | phenyl | 4-OMe-phenyl-CH₂— | CH | N | O—CH₂—CH₂—C | | O | O |
| I-356 | COOH | phenyl | 4-OMe-phenyl-CH₂— | CH | N | F | C—OMe | O | O |
| I-357 | COOH | phenyl | n-butyl | CH | N | Me | C-ethyl | N | — |
| I-358 | COOH | phenyl | ethyl | CH | N | Me | C—CH₂—OH | O | — |
| I-359 | COOH | phenyl | ethyl | CH | N | Me | C—N(CH₃)₂ | O | — |
| I-360 | COOH | phenyl | n-hexyl | CH | N | O—CH₂—O—C | | N | — |
| I-361 | COOH | 4-Me-phenyl | ethyl | CH | N | CH₂—CH₂—CH₂—C | | N | — |
| I-362 | COOH | phenyl | methyl | CH | N | CH₂—CH₂—O—C | | O | O |
| I-363 | COOH | phenyl | methyl | CH | N | F | C—OMe | O | O |
| I-364 | COOH | phenyl | ethyl | CH | N | CF₃ | C—N(CH₃)₂ | N | — |
| I-365 | COOH | phenyl | 4-OMe-phenyl-CH₂— | N | C-Me | Me | N | O | — |
| I-366 | COOH | phenyl | 4-OMe-phenyl-CH₂— | CH | N | Me | C-ethyl | O | O |
| I-367 | COOH | phenyl | 4-OMe-phenyl-CH₂— | CH | N | CH₂—CH₂—CH₂—C | | O | O |
| I-368 | COOH | phenyl | 3,4-di-Me-phenyl-CH₂— | N | C—OMe | Me | N | O | — |
| I-369 | COOH | phenyl | ethyl | CH | N | CH₂—CH₂—CH₂—C | | O | — |
| I-370 | COOH | phenyl | ethyl | CH | N | OMe | C-ethyl | O | — |
| I-371 | COOH | phenyl | 4-Me-phenyl-CH₂— | N | C—CH₂—CH₂—CH₂ | | N | O | — |
| I-372 | COOH | 4-OMe-phenyl | methyl | N | C-ethyl | Me | N | O | — |
| I-373 | COOH | phenyl | methyl | CH | N | CH₂—CH₂—CH₂—C | | O | O |
| I-374 | COOH | phenyl | methyl | CH | N | O—CH₂—CH₂—C | | O | O |
| I-375 | COOH | 4-OMe-phenyl | methyl | N | C—OMe | H | N | O | — |
| I-376 | COOH | phenyl | 4-i-propyl-phenyl-CH₂— | N | C—O—CH₂—O | | N | O | — |
| I-377 | COOH | phenyl | 4-OMe-phenyl-CH₂— | CH | N | Me | C—OMe | O | O |
| I-378 | COOH | phenyl | 4-OMe-phenyl-CH₂— | CH | N | F | C-Me | O | O |
| I-379 | COOH | phenyl | 3,4,5-tri-OMe-phenyl-CH₂— | N | C—O—CH₂—CH₂ | | N | O | — |
| I-380 | COOH | phenyl | ethyl | CH | N | Me | C-ethyl | O | — |
| I-381 | COOH | phenyl | ethyl | CH | N | O—CH₂—O—C | | O | — |
| I-382 | COOH | 4-OMe-phenyl | methyl | CH | CH | Me | N | O | — |
| I-383 | COOH | phenyl | 3,4,5-tri-OMe-phenyl-CH₂— | CH | C—N(CH₃)₂ | Me | N | O | — |
| I-384 | COOH | phenyl | methyl | CH | N | H | C—OMe | O | O |
| I-385 | COOH | phenyl | methyl | CH | N | O—CH₂—O—C | | O | O |
| I-386 | COOH | cyclohexyl | methyl | CH | C-Me | Me | N | O | — |
| I-387 | COOH | phenyl | 4-Me-phenyl-CH₂— | CH | C—OMe | Me | N | O | — |
| I-388 | COOH | phenyl | 4-OMe-phenyl-CH₂— | CH | C—N(CH₃)₂ | Me | N | O | O |
| I-389 | COOH | phenyl | 4-OMe-phenyl-CH₂— | CH | N | Me | C-Me | O | O |
| I-390 | COOH | phenyl | 2-OMe-phenyl-CH₂— | CH | C—OMe | OMe | N | O | — |
| I-391 | COOH | phenyl | ethyl | CH | N | Me | C—OMe | O | — |
| I-392 | COOH | phenyl | ethyl | CH | N | OMe | C-Me | O | — |
| I-393 | COOH | phenyl | 4-Cl-phenyl-CH₂— | CH | C—NH₂ | OMe | N | O | — |
| I-394 | COOH | phenyl | methyl | CH | C-ethyl | CF₃ | N | O | — |
| I-395 | COOH | phenyl | methyl | CH | N | OMe | C-Me | O | O |
| I-396 | COOH | phenyl | methyl | CH | N | Me | C-ethyl | O | O |
| I-397 | COOH | 4-OMe-phenyl | methyl | CH | C—OMe | H | N | O | — |
| I-398 | COOH | phenyl | 3,4-di-Cl-phenyl-CH₂— | CH | C—O—CH₂—O | | N | O | — |
| I-399 | COOH | phenyl | 4-OMe-phenyl-CH₂— | CH | C—O—CH₂—CH₂ | | N | O | O |
| I-400 | COOH | phenyl | 4-OMe-phenyl-CH₂— | CH | C—CH₂—OH | Me | N | O | O |
| I-401 | COOH | phenyl | cyclopentyl-CH₂— | CH | C—O—CH₂—CH₂ | | N | O | — |
| I-402 | COOH | phenyl | ethyl | CH | C—N(CH₃)₂ | Me | N | O | — |
| I-403 | COOH | phenyl | ethyl | CH | N | Me | C-Me | O | — |
| I-404 | COOH | 4-OMe-phenyl | methyl | CH | C-Me | F | N | O | — |
| I-405 | COOH | phenyl | 4-F-phenyl-CH₂— | CH | C—CH₂—CH₂—CH₂ | | N | O | — |
| I-406 | COOH | phenyl | methyl | CH | N | Me | C—OMe | O | O |
| I-407 | COOH | phenyl | methyl | CH | N | OMe | C—OMe | O | O |
| I-408 | COOH | phenyl | 4-Cl-phenyl-CH₂— | CH | C-ethyl | F | N | O | — |
| I-409 | COOMe | phenyl | methyl | CH | C—CH₂—OH | Me | N | O | — |
| I-410 | COOH | phenyl | 4-OMe-phenyl-CH₂— | CH | C—OMe | Me | N | O | O |
| I-411 | COOH | phenyl | 4-OMe-phenyl-CH₂— | CH | C—CH₂—CH₂—CH₂ | | N | O | O |
| I-412 | COOH | phenyl | phenyl-O—CH₂— | CH | C—N(CH₃)₂ | Me | N | O | — |
| I-413 | COOH | phenyl | ethyl | CH | C—CH₂—CH₂—CH₂ | | N | O | — |
| I-414 | COOH | phenyl | ethyl | CH | C—CH₂—OH | Me | N | O | — |

TABLE I-continued

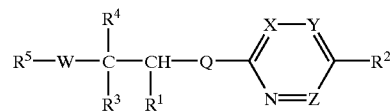

I

| No. | R¹ | R³, R⁴ | R⁵ | X | Y | R² | Z | Q | W |
|---|---|---|---|---|---|---|---|---|---|
| I-415 | COOH | phenyl | 4-Br-phenyl-CH$_2$— | CH | C—NH(CH$_3$) | OMe | N | O | — |
| I-416 | COOH | 4-OMe-phenyl | methyl | CH | N | Me | CH | O | — |
| I-417 | COOH | phenyl | methyl | CH | N | OMe | CH | O | O |
| I-418 | COOH | phenyl | methyl | CH | N | Me | C-Me | O | — |
| I-419 | COOH | phenyl | methyl | CH | N | CF$_3$ | C-Me | O | — |
| I-420 | COOH | phenyl | 4-OMe-phenyl-CH$_2$— | CH | N | Me | C—OMe | O | — |
| I-421 | COOH | phenyl | 4-OMe-phenyl-CH$_2$— | CH | C—NH(CH$_3$) | Me | N | O | O |
| I-422 | COOH | phenyl | 4-OMe-phenyl-CH$_2$— | CH | C-Me | Me | N | O | O |
| I-423 | COOH | phenyl | 3,4-dioxomethylenephenyl-CH$_2$— | CH | N | OMe | C-Me | O | — |
| I-424 | COOH | phenyl | ethyl | CH | C—O—CH$_2$—CH$_2$ | N | | O | — |
| I-425 | COOH | phenyl | ethyl | CH | C-Me | F | N | O | — |
| I-426 | COOH | phenyl | 3-Cl-phenyl-CH$_2$— | CH | N | Me | C-ethyl | O | — |
| I-427 | COOH | phenyl | methyl | CH | N | Me | C—OCF$_3$ | O | — |
| I-428 | COOH | phenyl | methyl | CH | C—NH(CH$_3$) | OMe | N | O | O |
| I-429 | COOH | phenyl | methyl | CH | N | Me | CH | O | — |
| I-430 | COOH | 4-OMe-phenyl | methyl | CH | N | | O—CH$_2$—O—C | O | — |
| I-431 | COOH | 4-Me-phenyl | methyl | CH | N | | CH$_2$—CH$_2$—CH$_2$—C | O | — |
| I-432 | COOH | phenyl | 4-OMe-phenyl-CH$_2$— | N | C-Me | ethyl | N | O | O |
| I-433 | COOH | phenyl | 4-OMe-phenyl-CH$_2$— | N | C—O—CH$_2$—O | N | | O | O |
| I-434 | COOH | phenyl | 2-Cl-phenyl-CH$_2$— | CH | N | | O—CH$_2$—CH$_2$—C | O | — |
| I-435 | COOH | phenyl | ethyl | CH | C-ethyl | Me | N | O | — |
| I-436 | COOH | phenyl | ethyl | CH | C—OMe | H | N | O | — |
| I-437 | COOH | phenyl | 3-OMe-phenyl-CH$_2$— | CH | N | | CH$_2$—CH$_2$—O—C | O | — |
| I-438 | COOH | phenyl | 3,5-di-OMe-phenyl-CH$_2$— | CH | N | F | C—OMe | O | — |
| I-439 | COOH | phenyl | methyl | CH | C—CH$_2$—OH | Me | N | O | O |
| I-440 | COOH | phenyl | methyl | CH | C—N(CH$_3$)$_2$ | Me | N | O | O |
| I-441 | COOH | 4-OMe-phenyl | methyl | CH | N | Me | C—NH(CH$_3$) | O | — |
| I-442 | COOH | phenyl | 2-Br-phenyl-CH$_2$— | CH | N | OMe | C-ethyl | O | — |
| I-443 | COOH | phenyl | 4-OMe-phenyl-CH$_2$— | N | C—OMe | Me | N | O | O |
| I-444 | COOH | phenyl | 4-OMe-phenyl-CH$_2$— | N | C—CH$_2$—CH$_2$—CH$_2$ | N | | O | O |
| I-445 | COOH | phenyl | 2-Cl-phenyl-CH$_2$— | CH | N | Me | C—CH$_2$—OH | O | — |
| I-446 | COOH | phenyl | ethyl | CH | C-OMe | Me | N | O | — |
| I-447 | COOH | phenyl | ethyl | CH | C—NH$_2$ | OMe | N | O | — |
| I-448 | COOH | phenyl | 4-i-propyl-phenyl-CH$_2$— | CH | N | Me | C—N(CH$_3$)$_2$ | O | — |
| I-449 | COOH | 4-OMe-phenyl | methyl | CH | N | OMe | C—NH(CH$_3$) | O | — |
| I-450 | COOH | phenyl | methyl | CH | C-Me | ethyl | N | O | O |
| I-451 | COOH | phenyl | methyl | CH | C-ethyl | OMe | N | O | O |
| I-452 | tetrazole | phenyl | ethyl | N | C-Me | Me | N | O | — |
| I-453 | COOH | phenyl | 3,4-di-OMe-phenyl-(CH$_2$)$_2$— | N | C—OMe | Me | N | O | — |
| I-454 | COOH | phenyl | 4-OMe-phenyl-(CH$_2$)$_2$— | CH | N | Me | C—N(CH$_3$)$_2$ | O | O |
| I-455 | COOH | phenyl | 4-OMe-phenyl-CH$_2$— | N | C-Me | Me | N | O | O |
| I-456 | COOH | phenyl | 3,4-di-OMe-phenyl-(CH$_2$)$_3$— | N | C—CH$_2$—CH$_2$—CH$_2$ | N | | O | — |
| I-457 | COOH | phenyl | ethyl | CH | C—N(CH$_3$)$_2$ | Me | N | O | — |
| I-458 | COOH | phenyl | ethyl | CH | C-Me | Me | N | O | — |
| I-459 | COOH | phenyl | 3,4-di-OMe-phenyl-(CH$_2$)$_3$— | N | C-ethyl | Me | N | O | — |
| I-460 | COOH | phenyl | 4-OMe-phenyl-(CH$_2$)$_3$— | CH | C—N(CH$_3$)$_2$ | Me | N | O | — |
| I-461 | COOH | phenyl | methyl | CH | C—O—CH$_2$—CH$_2$ | N | | O | O |
| I-462 | COOH | phenyl | methyl | CH | C—OMe | F | N | O | O |
| I-463 | COOH | phenyl | 3-Cl-phenyl-(CH$_2$)$_2$— | CH | C-Me | Me | N | O | — |
| I-464 | COOH | phenyl | 3,4-di-OMe-phenyl-(CH$_2$)$_3$— | CH | C—OMe | Me | N | O | — |
| I-465 | COOH | phenyl | 4-OMe-phenyl-(CH$_2$)$_2$— | CH | N | F | C—OMe | O | O |
| I-466 | COOH | phenyl | 4-OMe-phenyl-(CH$_2$)$_2$— | CH | N | Me | C—CH$_2$—OH | O | — |
| I-467 | COOH | phenyl | 3,4-di-OMe-phenyl-(CH$_2$)$_3$— | CH | C—NH$_2$ | OMe | N | O | — |
| I-468 | COOH | phenyl | ethyl | N | C—CH$_2$—CH$_2$—CH$_2$ | N | | O | — |
| I-469 | COOH | phenyl | ethyl | N | C-ethyl | Me | N | O | — |
| I-470 | COOH | phenyl | 4-Me-phenyl-(CH$_2$)$_3$— | CH | C-ethyl | Me | N | O | — |
| I-471 | COOH | phenyl | 4-OH-phenyl-(CH$_2$)$_3$— | CH | C—OMe | H | N | O | — |
| I-472 | COOH | phenyl | methyl | CH | C—OMe | H | N | O | O |
| I-473 | COOH | phenyl | methyl | CH | C—O—CH$_2$—O | N | | O | O |
| I-474 | COOH | phenyl | 4-OH-phenyl-(CH$_2$)$_2$— | CH | C—O—CH$_2$—CH$_2$ | N | | O | — |
| I-475 | COOH | phenyl | 3,4-dioxomethylenephenyl-(CH$_2$)$_2$— | CH | C-Me | F | N | O | — |
| I-476 | COOH | phenyl | 4-OMe-phenyl-(CH$_2$)$_2$— | CH | N | | CH$_2$—CH$_2$—CH$_2$—C | O | O |
| I-477 | COOH | phenyl | 4-OMe-phenyl-(CH$_2$)$_2$— | CH | N | | O—CH$_2$—CH$_2$—C | O | O |
| I-478 | COOH | phenyl | 4-Me-phenyl-(CH$_2$)$_2$— | CH | C—CH$_2$—CH$_2$—CH$_2$ | N | | O | — |
| I-479 | COOH | phenyl | ethyl | N | C-Me | Me | N | O | — |
| I-480 | COOH | phenyl | ethyl | N | C—OMe | Me | N | O | — |
| I-481 | COOH | phenyl | 2-Cl-phenyl-(CH$_2$)$_2$— | CH | C—CH$_2$—OH | Me | N | O | — |
| I-482 | COOH | phenyl | 3,5-di-OMe-phenyl-(CH$_2$)$_2$— | CH | C—N(CH$_3$)$_2$ | Me | N | O | — |
| I-483 | COOH | phenyl | methyl | CH | C-Me | OMe | N | O | O |

TABLE I-continued

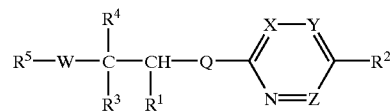

| No. | R¹ | R³, R⁴ | R⁵ | X | Y | R² | Z | Q | W |
|---|---|---|---|---|---|---|---|---|---|
| I-484 | COOH | phenyl | methyl | CH | C-ethyl | Me | N | O | O |
| I-485 | COOH | phenyl | HO—CH₂—CH₂— | CH | N | Me | C-Me | O | — |
| I-486 | COOH | phenyl | HO—CH₂—CH₂— | CH | N | Me | C—OMe | O | — |
| I-487 | COOH | phenyl | 4-OMe-phenyl-(CH₂)₂— | CH | N | F | C-Me | O | O |
| I-488 | COOH | phenyl | 4-OMe-phenyl-(CH₂)₂— | CH | N | Me | C-ethyl | O | O |
| I-489 | COOH | phenyl | HO—CH₂—CH₂— | CH | N | OMe | C-Me | O | — |
| I-490 | COOH | phenyl | methyl | CH | N | Me | C—N(CH₃)₂ | O | — |
| I-491 | COOH | phenyl | methyl | CH | N | OMe | C—NH(CH₃) | O | — |
| I-492 | COOH | phenyl | ethyl | CH | N | CF₃ | C-ethyl | O | — |
| I-493 | COOH | 4-OMe-phenyl | ethyl | CH | N | O—CH₂—O—C | | O | — |
| I-494 | COOH | phenyl | methyl | CH | C—OMe | Me | N | O | O |
| I-495 | COOH | phenyl | methyl | CH | C—OMe | OMe | N | O | O |
| I-496 | COOH | phenyl | 4-Br-phenyl-(CH₂)₂— | CH | N | C—CH₂—CH₂—CH₂ | | O | — |
| I-497 | COOH | phenyl | 4-OH-phenyl-(CH₂)₂— | CH | N | OMe | C-ethyl | O | — |
| I-498 | COOH | phenyl | 4-OMe-phenyl-(CH₂)₂— | CH | N | Me | C-Me | O | O |
| I-499 | COOH | phenyl | 4-OMe-phenyl-(CH₂)₂— | CH | N | Me | C—OMe | O | O |
| I-500 | COOH | phenyl | 3,4-di-OMe-phenyl-(CH₂)₃— | CH | N | Me | C—CH₂—OH | O | — |
| I-501 | COOH | phenyl | methyl | CH | N | OMe | C-ethyl | O | — |
| I-502 | COOH | phenyl | methyl | CH | N | Me | C—CH₂—OH | O | — |
| I-503 | COOHI | phenyl | 3,4-di-OMe-phenyl-(CH₂)₃— | CH | N | Me | C—N(CH₃)₂ | O | — |
| I-504 | COOH | phenyl | propyl | CH | N | OMe | C—NH(CH₃) | O | — |
| I-505 | COOH | phenyl | methyl | CH | CH | OMe | N | O | O |
| I-506 | COOH | phenyl | methyl | CH | C-Me | Me | N | O | O |
| I-507 | COOH | phenyl | HO—CH₂—CH₂— | N | C-Me | Me | N | O | — |
| I-508 | COOH | phenyl | HO—CH₂—CH₂— | N | C—OMe | Me | N | O | — |
| I-509 | COOH | phenyl | 4-OMe-phenyl-(CH₂)₂— | CH | C—CH₂—OH | Me | N | O | O |
| I-510 | COOH | phenyl | 4-OMe-phenyl-(CH₂)₂— | CH | C—N(CH₃)₂ | Me | N | O | O |
| I-511 | COOH | 4-OMe-phenyl | HO—CH₂— | N | C—CH₂—CH₂—CH₂ | | N | O | — |
| I-512 | COOH | phenyl | methyl | CH | N | F | C—OMe | O | — |
| I-513 | COOH | phenyl | methyl | CH | N | Me | C—NH(CH₃) | O | — |
| I-514 | COOH | phenyl | HO—CH₂— | N | C-ethyl | CF₃ | N | O | — |
| I-515 | COOH | phenyl | propyl | CH | C-Me | Me | N | O | — |
| I-516 | COOH | phenyl | methyl | N | C—O—CH₂—CH₂ | | N | O | O |
| I-517 | COOH | phenyl | methyl | CH | CH | Me | N | O | O |
| I-518 | COOH | phenyl | butyl | CH | C—OMe | Me | N | O | — |
| I-519 | COOH | phenyl | i-butyl | CH | C-ethyl | Me | N | O | — |
| I-520 | COOH | phenyl | 4-OMe-phenyl-(CH₂)₂— | CH | C—CH₂—CH₂—CH₂ | | N | O | O |
| I-521 | COOH | phenyl | 4-OMe-phenyl-(CH₂)₂— | CH | C—O—CH₂—CH₂ | | N | O | O |
| I-522 | COOH | phenyl | propyl | CH | C—OMe | H | N | O | — |
| I-523 | COOH | phenyl | methyl | CH | N | O—CH₂—CH₂—C | | O | — |
| I-524 | COOH | phenyl | methyl | CH | N | CH₂—CH₂—O—C | | O | — |
| I-525 | COOH | phenyl | HO—CH₂—CH₂— | CH | C—O—CH₂—CH₂ | | N | O | — |
| I-526 | COOH | phenyl | 4-OMe-phenyl-CH₂—O—CH₂— | CH | C—CH₂—CH₂—CH₂ | | N | O | — |
| I-527 | COOH | phenyl | methyl | N | C—OMe | H | N | O | O |
| I-528 | COOH | phenyl | methyl | N | C—O—CH₂—O | | N | O | O |
| I-529 | COOH | phenyl | 4-OMe-phenyl-CH₂—O—CH₂— | CH | N | Me | C-Me | O | — |
| I-530 | COOH | phenyl | 3,4-di-OMe-phenyl-CH₂—O—CH₂— | CH | N | Me | C—OMe | O | — |
| I-531 | COOH | phenyl | 4-OMe-phenyl-(CH₂)₂— | CH | C-Me | Me | N | O | O |
| I-532 | COOH | phenyl | 4-OMe-phenyl-(CH₂)₂— | CH | C—OMe | Me | N | O | O |
| I-533 | COOH | phenyl | 3,4-di-OMe-phenyl-CH₂—O—CH₂— | CH | N | OMe | C-Me | O | — |
| I-534 | COOH | phenyl | methyl | CH | N | O—CH₂—O—C | | O | — |
| I-535 | COOH | phenyl | methyl | CH | N | CH₂—CH₂—CH₂—C | | O | — |
| I-536 | COOH | phenyl | 4-Cl-phenyl-CH₂—O—CH₂— | CH | N | Me | C-ethyl | O | — |
| I-537 | COOH | phenyl | HO—CH₂—CH₂— | CH | N | O—CH₂—O—C | | O | — |
| I-538 | COOH | phenyl | methyl | N | C-Me | OMe | N | O | O |
| I-539 | COOH | phenyl | methyl | N | C-ethyl | Me | N | O | O |
| I-540 | COOH | phenyl | phenyl-CH₂—O—CH₂— | CH | N | CH₂—CH₂—CH₂—C | | O | — |
| I-541 | COOH | phenyl | 4-OMe-phenyl-(CH₂)₂— | N | C—O—CH₂—O | | N | O | O |
| I-542 | COOH | phenyl | 4-OMe-phenyl-(CH₂)₂— | CH | C—NH(CH₃) | Me | N | O | O |
| I-543 | COOH | phenyl | HO—CH₂— | CH | N | CF₃ | C-ethyl | O | — |
| I-544 | COOH | phenyl | propyl | CH | N | Me | C—N(CH₃)₂ | O | — |
| I-545 | COOH | phenyl | methyl | N | C-Me | Me | N | O | O |
| I-546 | COOH | phenyl | methyl | N | C—OMe | Me | N | O | O |
| I-547 | COOH | phenyl, naphthyl | methyl | CH | N | Me | C-Me | O | O |
| I-548 | COOH | phenyl-4-Cl-phenyl | ethyl | CH | N | CF₃ | C-ethyl | O | O |
| I-549 | COOH | 4-F-phenyl, 4-Cl-phenyl | propyl | CH | C-ethyl | Me | N | O | O |

TABLE I-continued $$R^5-W-\underset{\underset{R^3}{|}}{\overset{\overset{R^4}{|}}{C}}-\underset{\underset{R^1}{|}}{CH}-Q-\begin{array}{c}X-Y\\ \| \ \ \| \\ N=Z\end{array}-R^2 \qquad I$$

| No. | $R^1$ | $R^3$, $R^4$ | $R^5$ | X | Y | $R^2$ | Z | Q | W |
|---|---|---|---|---|---|---|---|---|---|
| I-550 | COOH | naphthyl, 4-Cl-phenyl | methyl | CH | C—OMe | Me | N | O | O |
| I-551 | COOH | 4-Me-phenyl, phenyl | 3,4-di-OMe-phenyl-$(CH_2)_2$— | CH | C-Me | H | N | O | O |
| I-552 | COOH | naphthyl, naphthyl | methyl | CH | C—$CH_2$—$CH_2$—$CH_2$ | | N | O | O |

The compounds of the present invention offer a new therapeutic potential for the treatment of hypertension, pulmonary high blood pressure, myocardial infarct, angina pectoris, arrhythmia, acute/chronic kidney failure, chronic cardiac insufficiency, renal insufficiency, cerebral vasospasms, cerebral ischemia, subarachnoid hemorrhages, migraine, asthma, atherosclerosis, endotoxic shock, endotoxin-induced organ failure, intravascular coagulation, restenosis after angioplasty and bypass operations, benign prostate hyperplasia, ischemic kidney failure and kidney failure or hypertension caused by intoxication, metastasis and growth of mesenchymal tumors such as prostate carcinoma, contrast agent-induced kidney failure, pancreatitis, gastrointestinal ulcers.

The invention further relates to combinations of endothelin receptor antagonists of the formula I and inhibitors of the renin-angiotensin system. Inhibitors of the renin-angiotensin system are renin inhibitors, angiotensin II antagonists and angiotensin-converting enzyme (ACE) inhibitors. Combinations of endothelin receptor antagonists of the formula I and ACE inhibitors are preferred.

The invention further relates to combinations of endothelin receptor antagonists of the formula I and calcium antagonists such as verapamil.

The invention further relates to combinations of endothelin receptor antagonists of the formula I and beta-blockers.

The invention further relates to combinations of endothelin receptor antagonists of the formula I and diuretics.

The invention further relates to combinations of endothelin receptor antagonists of the formula I and substances which block the action of VEGF (vascular endothelial growth factor). Substances of this type are, for example, antibodies directed against VEGF or specific binding proteins or alternatively low molecular weight substances which can specifically inhibit VEGF release or receptor binding.

The abovementioned combinations can be administered simultaneously or sequentially one after the other. They can be employed either in a single pharmaceutical formulation or alternatively in separate formulations. The administration form can also be different, for example the endothelin receptor antagonists can be administered orally and VEGF inhibitors can be administered parenterally.

These combination preparations are especially suitable for the treatment and prevention of hypertension and its sequelae, and for the treatment of cardiac insufficiency.

The good action of the compounds can be shown in the following experiments:

Receptor binding studies

For binding studies cloned human $ET_A$- or $ET_B$ receptor-expressing CHO cells were employed.

Membrane preparation

The $ET_A$ or $ET_B$ receptor-expressing CHO cells were proliferated in DMEM NUT MIX $F_{12}$ medium (Gibco, No. 21331–020) with 10% fetal calf serum (PAA Laboratories GmbH, Linz, No. A15–022), 1 mM glutamine (Gibco No. 25030–024), 100 U/ml of penicillin and 100 µg/ml of streptomycin (Sigma No P 0781). After 48 hours, the cells were washed with PBS and incubated for 5 minutes at 37° C. with 0.05% trypsin-containing PBS. The mixture was then neutralized with medium and the cells collected by centrifugation at 300 x g.

For the membrane preparation, the cells were adjusted to a concentration of $10^8$ cells/ml of buffer (50 mM tris HCL buffer, pH 7.4) and then disintegrated by ultrasound Branson Sonifier 250, 40–70 seconds/constant/output [sic] 20).

Binding tests

For the $ET_A$ and $ET_B$ receptor binding test, the membranes were suspended in an incubation buffer (50 mM tris $HC_1$, pH 7.4 with 5 mM $MnCl_2$40 mg/ml of bacitracin and 0.2% BSA) in a concentration of 50 µg of protein per test batch and incubated at 25° C. with 25 pM [$^{125}$I]-$ET_1$ ($ET_A$ receptor test) or 25 pM [$^{125}$I]-$ET_3$ ($ET_B$ receptor test) in the presence and absence of test substance. The nonspecific binding was determined with $10^{-7}$ M $ET_1$. After 30 min, the free and the bound radioligand were separated by filtration through GF/B glass fiber filters (Whatman, England) on a Skatron cell collector (Skatron, Lier, Norway) and the filters were washed with ice-cold tris HCl buffer, pH 7.4 with 0.2% BSA.

The radioactivity collected on the filters was quantified using a Packard 2200 CA liquid scintillation counter.

Testing of the ET antagonists in vivo:

Male SD rats 250–300 g in weight were anesthetized with amobarbital, artificially respirated, vagotomized and pithed. The carotid artery and jugular vein were catheterized.

In control animals, the intravenous administration of 1 mg/kg of $ET_1$ [sic] leads to a marked blood pressure increase, which lasts for a relatively long period of time.

The test animals were injected i.v. (1 ml/kg) with the test compounds 30 min before ET1 [sic] administration. To determine the ET-antagonistic properties, the blood pressure changes in the test animals were compared with those in the control animals.

p.o. Testing of the ET receptor antagonists:

Male normotensive rats (Sprague Dawley, Janvier) 250–350 g in weight are orally pretreated with the test substances. 80 minutes later, the animals are anesthetized with urethane and the carotid artery (for blood pressure measurements) and the jugular vein (administration of big endothelin/endothelin 1) are catheterized.

After a stabilization phase, big endothelin (20 µg/kg, administration vol. 0.5 ml/kg) or ET1 [sic] (0.3 µg/kg, administration vol. 0.5 ml/kg) is given intravenously. Blood pressure and heart rates are recorded continuously for 30 minutes. The marked and long-lasting blood pressure changes are calculated as the area under the curve (AUC). To determine the antagonistic action of the test substances, the AUCs of the substance-treated animals are compared with the AUC of the control animals.

The compounds according to the invention can be administered orally or parenterally (subcutaneously, intravenously, intramuscularly, intraperitoneally) in a customary manner. Administration can also be carried out through the nasopharynx using vapors or sprays.

The dosage depends on the age, condition and weight of the patient and on the type of administration. As a rule, the daily dose of active compound is from approx. 0.5 to 100 mg/kg of body weight in the case of oral administration and from approx. 0.1 to 30 mg/kg of body weight in the case of parenteral administration.

The novel compounds can be used liquid or solid in the customary pharmaceutical administration forms, eg. as tablets, film-coated tablets, capsules, powders, granules, coated tablets, suppositories, solutions, ointments, creams or sprays. These are prepared in a customary manner. The active compounds can in this case be processed with the customary pharmaceutical auxiliaries such as tablet binders, fillers, preservatives, tablet disintegrants, flow-regulating agents, plasticizers, wetting agents, dispersants, emulsifiers, solvents, release-delaying agents, antioxidants and/or propellants (cf. H. Sucker et al.: Pharmazeutische Technologie [Pharmaceutical Technology], Thieme-Verlag, Stuttgart, 1991). The administration forms thus obtained normally contain the active compound in an amount from 0.1 to 90% by weight.

We claim:

1. A compound of formula I

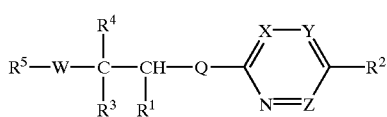

where
$R^1$ is tetrazole or a group

where R has the following meanings:
a) a radical $OR^6$ where $R^6$ is:
  hydrogen, the cation of an alkali metal, the cation of an alkaline earth metal of a physiologically tolerable organic ammonium ion;
  $C_3$–$C_8$-cycloalkyl, $C_1$–$C_8$-alkyl,
  unsubstituted or substituted $CH_2$-phenyl,
  unsubstituted or substituted $C_3$–$C_8$-alkenyl or $C_3$–$C_8$-alkynyl or
  unsubstituted or substituted phenyl;
b) a 5-membered heteroaromatic linked via a nitrogen atom;

c) a group

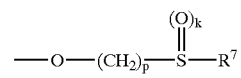

where k can assume the values of 0, 1 and 2, p the values 1, 2, 3 and 4 and $R^7$ is $C_1$–$C_4$-alkyl, $C_3$–$C_8$-cycloalkyl, $C_3$–$C$,-alkenyl, $C_3$–$C_8$-alkynyl or unsubstituted or substituted phenyl;
d) a radical

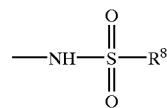

where $R^8$ is $C_1$–$C_4$-alkyl, $C_3$–$C_8$-alkenyl, $C_3$–$C_8$-alkynyl, $C_3$–$C_8$-cycloalkyl, it being possible for these radicals to carry a $C_1$–$C_4$-alkoxy, $C_1$–$C_4$-alkylthio and/or a phenyl radical; $C_1$–$C_4$-haloalkyl or unsubstituted or substituted phenyl;

X is nitrogen or methine;
Y is nitrogen if X is methine and Y is $CR^9$ if X is nitrogen;
Z is nitrogen;
$R^2$ is $C_1$–$C_4$-alkyl, $C_2$–$C_4$-alkenyl, $C_2$–$C_4$-alkynyl, it being possible for these radicals to be unsubstituted or substituted; hydrogen, halogen, $C_1$–$C_4$-alkoxy, $C_1$–$C_4$-haloalkyl, $C_3$–$C_6$-alkenyloxy, $C_3$–$C_6$-alkynyloxy, $C_1$–$C_4$-alkylthio, $C_1$–$C_4$-alkylcarbonyl, $C_1$–$C_4$-alkoxycarbonyl, $NH(C_1$–$C_4$-alkyl), $N(C_1$–$C_4$-alkyl$)_2$, hydroxyl, carboxyl, amino; or
$CR^2$ together with $CR^9$ forms a 5- or 6-membered alkylene or alkenylene ring which can be unsubstituted or substituted, and where in each case one or more methylene group can be replaced by oxygen, sulfur, —NH or $N(C_1$–$C_4$-alkyl);
$R^3$ and $R^4$ (which can be identical or different) are:
  phenyl or naphthyl, unsubstituted or substituted, or phenyl or naphthyl which are connected to one another in the ortho position via a direct bond, a methylene, ethylene or ethenylene group, an oxygen or sulfur atom or an $SO_2$—, NH— or N-alkyl group;
  unsubstituted or substituted $C_3$–$C_8$-cycloalkyl;
$R^5$ is hydrogen, $C_1$–$C_8$-alkyl, $C_3$–$C_8$-alkenyl or $C_3$–$C_8$-alkynyl, it being possible for these radicals to be unsubstituted or substituted;
  unsubstituted or substituted phenyl or naphthyl;
  a 5- or 6-membered heteroaromatic, having one to three nitrogen atoms and/or a sulfur or oxygen atom, and which can be unsubstituted or substituted;
  unsubstituted or substituted $C_3$–$C_8$-cycloalkyl;
$R^9$ is hydrogen, hydroxyl, $NH_2$, $NH(C_1$–$C_4$-alkyl), $N(C_1$–$C_4$-alkyl$)_2$, halogen, $C_1$–$C_4$-alkoxy, $C_1$–$C_4$-haloalkoxy or $C_1$–$C_4$-alkylthio;
  $C_1$–$C_4$-alkyl, $C_2$–$C_4$-alkenyl, $C_2$–$C_4$-alkynyl, it being possible for these radicals to be unsubstituted or substituted;
  or $CR^9$ is linked with $CR^2$ as indicated above to give a 5- or 6-membered ring;
W is sulfur, oxygen or a single bond;
Q is oxygen or NH, with the proviso that if Q=NH, then W is a single bond or the physiologically tolerable salts, or the enantiomerically pure and diastereomerically pure forms.

2. A drug preparation for oral and parenteral administration, comprising per individual dose, customary drug auxiliaries, and at least one compound of formula I as claimed in claim 1.

3. A combination of the compound of formula I as claimed in claim 1 and one or more active compounds selected from inhibitors of the renin-angiotensin system.

4. The combination claimed in claim 3, wherein the inhibitors of the renin-angiotensin system are renin inhibitors, angiotensin II antagonists, angiotensin-converting enzyme (ACE) inhibitors, mixed ACE/neutral endopeptidase (NEP) inhibitors β-blockers, diuretics, calcium antagonists and VEGF-blocking substances.

5. A method of treating high blood pressure, pulmonary high blood pressure, myocardial infarct, angina pectoris, restenosis, arrhythmia, acute/chronic kidney failure, chronic cardiac insufficiency, renal insufficiency, cerebral vasospasms, cerebral ischemia, subarachnoid hemorrhages, migraine, asthma, atherosclerosis, endotoxic shock, endotoxin-induced kidney failure, kidney failure or hypertension caused by intoxication, metastasis and growth of mesenchymal tumors, contrast agent-induced kidney failure, pancreatitis, gastrointestinal ulcers, stroke, benign prostate hyperplasia or Raynaud's Syndrome caused or aggravated by abnormal release of endothelin, said method comprising administering to a human or animal in need of such treatment an effective amount of the compound of formula I as claimed in claim 1.

6. The method of treating illnesses as defined in claim 5, wherein said illness is selected from the group consisting of chronic cardiac insufficiency, restenosis, high blood pressure, pulmonary high blood pressure, acute/chronic kidney failure, cerebral ischemia and benign prostate hyperplasia.

\* \* \* \* \*

UNITED STATES PATENT AND TRADEMARK OFFICE
CERTIFICATE OF CORRECTION

PATENT NO.    : 6,448,248 B1
DATED         : September 10, 2002
INVENTOR(S)   : Amberg et al.

It is certified that error appears in the above-identified patent and that said Letters Patent is hereby corrected as shown below:

Column 30,
Line 8, "$C_3$-$C_{,}$-" should be -- $C_3$-$C_8$- --.

Signed and Sealed this

Fourteenth Day of January, 2003

JAMES E. ROGAN
*Director of the United States Patent and Trademark Office*